(12) United States Patent
Matsukuma et al.

(10) Patent No.: US 9,834,813 B2
(45) Date of Patent: Dec. 5, 2017

(54) METHOD FOR DETECTING MUTANT DNA

(75) Inventors: Shoichi Matsukuma, Kanagawa (JP); Tomokazu Ishikawa, Hyogo (JP)

(73) Assignees: Wako Pure Chemical Industries, Ltd., Osaka (JP); Kanagawa Prefectural Hospital Organization, Kanagawa (JP)

( * ) Notice: Subject to any disclaimer, the term of this patent is extended or adjusted under 35 U.S.C. 154(b) by 110 days.

(21) Appl. No.: 13/825,223

(22) PCT Filed: Sep. 22, 2011

(86) PCT No.: PCT/JP2011/071721
§ 371 (c)(1),
(2), (4) Date: Mar. 20, 2013

(87) PCT Pub. No.: WO2012/039481
PCT Pub. Date: Mar. 29, 2012

(65) Prior Publication Data
US 2013/0217016 A1  Aug. 22, 2013

(30) Foreign Application Priority Data

Sep. 22, 2010 (JP) .................... 2010-212807
Mar. 11, 2011 (JP) .................... 2011-053901

(51) Int. Cl.
| | | |
|---|---|---|
| *C12Q 1/68* | (2006.01) | |
| *C12P 19/34* | (2006.01) | |
| *G01N 33/00* | (2006.01) | |
| *C07H 21/02* | (2006.01) | |
| *C07H 21/04* | (2006.01) | |
| *B01D 57/02* | (2006.01) | |
| *B01D 59/42* | (2006.01) | |
| *B01D 59/50* | (2006.01) | |
| *B01D 61/42* | (2006.01) | |
| *B01D 61/58* | (2006.01) | |

(52) U.S. Cl.
CPC .................. *C12Q 1/6827* (2013.01)

(58) Field of Classification Search
USPC ............ 435/6.1, 6.11, 6.12, 91.1, 91.2, 183; 436/94, 501; 536/23.1, 24.3, 24.33, 25.3; 204/450, 451, 456
See application file for complete search history.

(56) References Cited

FOREIGN PATENT DOCUMENTS

JP  2007-61080  3/2007

OTHER PUBLICATIONS

M. Orita et al., "Rapid and Sensitive Detection of Point Mutations and DNA Polymorphisms Using the Polymerase Chain Reaction," Genomics 5, pp. 874-879 (1989).
S. Matsukuma et al., "Rapid and Simple Detection of Hot Spot Point Mutations of Epidermal Growth Factor Receptor, BRAF, and NRAS in Cancers Using the Loop-Hybrid Mobility Shift Assay", Journal of Molecular Diagnostics, vol. 8, No. 4, pp. 504-512 (2006).
S. Matsukuma, "Loop Hetero Duplex DNA no PAGE deno Kyodo Henka o Rip Shita Idenshi Hen'l Kenshutsu", The Physico-Chemical Biology, vol. 52, No. 3, p. 75 (2008).
English-language International Search Report from the Japanese Patent Office in International Application. No. PCT/JP2011/071721, dated Dec. 6, 2011.

*Primary Examiner* — Frank Lu
(74) *Attorney, Agent, or Firm* — White & Case LLP

(57) ABSTRACT

The present invention relates to a method for detecting of a mutant DNA using a probe, comprising:

(1) contacting a sample containing a single-stranded DNA which has a substituted nucleotide, a deleted nucleotide region, or an inserted nucleotide region (mutant-type DNA), or/and a wild-type single-stranded DNA (wild-type DNA) corresponding thereto with the probe which hybridizes with both single-stranded DNA, to form a hybrid with the mutant-type DNA (mutant-type hybrid) or/and a hybrid with a wild-type DNA (wild-type hybrid), wherein at least one of the obtained mutant-type hybrid and wild-type hybrid has the stem structure;

(2) separating the obtained mutant-type hybrid or/and wild-type hybrid by electrophoresis on the basis of presence or absence of the stem structure or difference in the stem structure; and (3) detecting the presence or absence of the mutant-type DNA in the sample.

15 Claims, 9 Drawing Sheets

[codon 12]
1. KR12_CG
2. KR12_TG
3. KR12_GA
4. KR12_GC
5. KR12_GT

[codon 13]
6. KR13_CG
7. KR12_TG
WT. GGC codon12
1 : KR12_AG
2 : KR12_CG
3 : KR12_TG
4 : KR12_GA
5 : KR12_GC
6 : KR12_GT codon13
7 : KR13_AG
8 : KR13_CG
9 : KR13_TG
10 : KR13_GA
11 : KR13_GC
12 : KR13_GT lane  mutant-type
1. (TA)5
2. (TA)6
3. (TA)7
4. (TA)8

Fig. 12

|  |  | Mutant-type DNA | Wild-type DNA |
|---|---|---|---|
| I-1-a1 | Probe | 3-1stSS-X-N'-St-X-2ndSS-5 | 3-1stSS-X-N'-St-X-2ndSS-5 |
|  | Genome | 5-1stDS-X-M------X-2ndDS-3 | 5-1stDS-X-N------X-2ndDS-3 |
| I-1-a2 | Probe | 3-1stSS-X-N'-X-St-X-2ndSS-5 | 3-1stSS-X-N'-X-St-X-2ndSS-5 |
|  | Genome | 5-1stDS-X-M -X----X-2ndDS-3 | 5-1stDS-X-N -X-----X-2ndDS-3 |
| I-1-a3 | Probe | 3-1stSS-X-N'-X-X-St-X-2ndSS-5 | 3-1stSS-X-N'-X-X-St-X-2ndSS-5 |
|  | Genome | 5-1stDS-X-M -X-X-----X-2ndDS-3 | 5-1stDS-X-N -X-X-----X-2ndDS-3 |
| I-1-a4 | Probe | 3-1stSS-X-St-N'-X-2ndSS-5 | 3-1stSS-X-St-N-X-2ndSS-5 |
|  | Genome | 5-1stDS-X-----M -X-2ndDS-3 | 5-1stDS-X-----N-X-2ndDS-3 |
| I-1-a5 | Probe | 3-1stSS-X-St-X-N'-X-2ndSS-5 | 3-1stSS-X-St-X-N'-X-2ndSS-5 |
|  | Genome | 5-1stDS-X-----X-M -X-2ndDS-3 | 5-1stDS-X-----X-N -X-2ndDS-3 |
| I-1-a6 | Probe | 3-1stSS-X-St-X-X-N'-X-2ndSS-5 | 3-1stSS-X-St-X-X-N'-X-2ndSS-5 |
|  | Genome | 5-1stDS-X----X-X-M -X-2ndDS-3 | 5-1stDS-X----X-X-N -X-2ndDS-3 |

Fig. 13

|  |  | Mutant-type DNA | Wild-type DNA |
|---|---|---|---|
| I-1-b1 | Probe | 3-1stSS-X-M'-St-X-2ndSS-5 | 3-1stSS-X-M'-St-X-2ndSS-5 |
|  | Genome | 5-1stDS-X-M------X-2ndDS-3 | 5-1stDS-X-N------X-2ndDS-3 |
| I-1-b2 | Probe | 3-1stSS-X-M'-X-St-X-2ndSS-5 | 3-1stSS-X-M'-X-St-X-2ndSS-5 |
|  | Genome | 5-1stDS-X-M -X-----X-2ndDS-3 | 5-1stDS-X-N -X----X-2ndDS-3 |
| I-1-b3 | Probe | 3-1stSS-X-M'-X-X-St-X-2ndSS-5 | 3-1stSS-X-M'-X-X-St-X-2ndSS-5 |
|  | Genome | 5-1stDS-X-M -X-X-----X-2ndDS-3 | 5-1stDS-X-N -X-X-----X-2ndDS-3 |
| I-1-b4 | Probe | 3-1stSS-X-St-M'-X-2ndSS-5 | 3-1stSS-X-St-M'-X-2ndSS-5 |
|  | Genome | 5-1stDS-X-----M-X-2ndDS-3 | 5-1stDS-X-----N -X-2ndDS-3 |
| I-1-b5 | Probe | 3-1stSS-X-St-X-M'-X-2ndSS-5 | 3-1stSS-X-St-X-M'-X-2ndSS-5 |
|  | Genome | 5-1stDS-X-----X-M -X-2ndDS-3 | 5-1stDS-X-----X-N -X-2ndDS-3 |
| I-1-b6 | Probe | 3-1stSS-X-St-X-X-M'-X-2ndSS-5 | 3-1stSS-X-St-X-X-M'-X-2ndSS-5 |
|  | Genome | 5-1stDS-X-----X-X-M-X-2ndDS-3 | 5-1stDS-X-----X-X-N-X-2ndDS-3 |

Fig. 14

| | | Mutant-type DNA | Wild-type DNA |
|---|---|---|---|
| I-2-a1 | Probe | 3-1stSS-X-N'-------X-2ndSS-5 | 3-1stSS-X-N'-------X-2ndSS-5 |
| | Genome | 5-1stDS-X-M-(St)-X-2ndDS-3 | 5-1stDS-X-N-(St)-X-2ndDS-3 |
| I-2-a2 | Probe | 3-1stSS-X-------N'-X-2ndSS-5 | 3-1stSS-X-------N'-X-2ndSS-5 |
| | Genome | 5-1stDS-X-(St)-M-X-2ndDS-3 | 5-1stDS-X-(St)-N-X-2ndDS-3 |

Fig. 15

| | | Mutant-type | Wild-type |
|---|---|---|---|
| I-2-b1 | Probe | 3-1stSS-X-M'-------X-2ndSS-5 | 3-1stSS-X-M'-------X-2ndSS-5 |
| | Genome | 5-1stDS-X-M-(St)-X-2ndDS-3 | 5-1stDS-X-N-(St)-X-2ndDS-3 |
| I-2-b2 | Probe | 3-1stSS-X-------M'-X-2ndSS-5 | 3-1stSS-X-------M'-X-2ndSS-5 |
| | Genome | 5-1stDS-X-(St)-M-X-2ndDS-3 | 5-1stDS-X-(St)-N-X-2ndDS-3 |

Fig. 16
IN-1
loop sequence 5'tatatatata3'
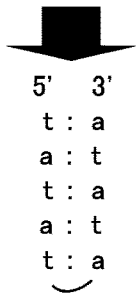
```
5'   3'
 t : a
 a : t
 t : a
 a : t
 t : a
```
Fig. 17
Fig. 18
5' ttctgcagaa 3'
```
5' 3'
t : a
t : a
c : g
t : a
 gc
```
Fig. 19
loop-out seq.
3' ggtatatata 5'
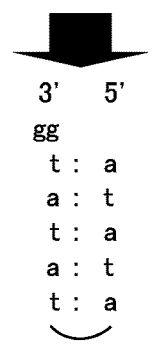
```
3'   5'
gg
 t : a
 a : t
 t : a
 a : t
 t : a
```
Fig. 20
loop-out seq.
3' ggtatatatata 5'
```
3'   5'
gg
 t : a
 a : t
 t : a
 a : t
 t : a
 a : t
```
Fig. 21
loop-out seq.
3' ggtata 5'
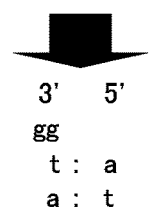
```
3'   5'
gg
 t : a
 a : t
```

METHOD FOR DETECTING MUTANT DNA

TECHNICAL FIELD

The present invention relates to a method for detecting of a mutant DNA (a mutant type DNA), wherein a hybrid of double-stranded DNA having a characteristic shape is formed by hybridizing the single-stranded DNA with a probe, and by separating the obtained hybrid by electrophoresis based on said characteristic shape, the mutant-type DNA is detected.

BACKGROUND ART

In recent years, presence or absence of mutation in a particular gene has been emphasized in various fields. For example, in DNA identification in forensics, determination of presence or absence of one nucleotide substitution by mutation or polymorphism in DNA is already well known as an individual identification technique. In addition, also in the medical field, correlation between specific genetic polymorphisms and drug susceptibility has become known, and trials to reduce the risk of drug-induced health disaster by investigating specific genetic polymorphisms have been done. Moreover, the detection of mutation in the gene is also employed for detection etc. of a mutant-type DNA holder of a hereditary disorder and its importance is increasing rather than before.

As for the conventional simple method for detecting single nucleotide substitution in DNA, SSCP method has been known. The SSCP method is a method through the use of a fact that DNA fragment is amplified by polymerase chain reaction (PCR) method, and the amplified product is made to the single-stranded DNA by thermal melting, and in the cooling process after thermal melting, said single-stranded DNA forms base-pairs partially within a molecule; and in this method, the molecule having single nucleotide mutation is changed to the shape of the single-stranded DNA, and based on the difference of mobility of electrophoresis from a wild-type DNA, separation and discrimination of the mutant-type DNA is performed. However, to maintain the molecular shape of single-strand DNA, this SSCP method needed to keep the temperature constant during electrophoresis. Therefore, the electrophoresis equipment is required to be provided with a circulation type constant temperature system, and remained a problem that a big unit would be needed.

And, as a method for solving the above-described problem on the SSCP method, a loop hybrid (LH) method in which single-stranded oligo DNA is added to the reaction solution after the PCR reaction of DNA fragment to hybridize with DNA fragment, and the mutant-type DNA is discriminated by electrophoresis on the basis of the structural difference of the obtained hybrid, has been proposed (JP-A-2007-61080).

Non-patent Literature 1: Orita, M. et al., Genomics 5, 874-879 (1989);
Non-patent Literature 2: Matsukuma, S. et al., J. Mol. Diag. 8, 504-512 (2006);
Patent Literature 1: JP-A-2007-61080.

DISCLOSURE OF THE INVENTION

Problem to be Solved by the Invention

The present inventors have found that in the above-described LH method, separation of the mutant-type DNA from the wild-type DNA by electrophoresis was incomplete and sometimes the mutant-type DNA could not be detected, and have further investigated intensively to develop a method which can separate the wild-type DNA and the mutant-type DNA completely and can detect the mutant-type DNA with high accuracy. As a result, it was found that, by making the loop portion in the hybrid obtained by LH method the stem structure, the hybrid derived from the wild-type DNA and the hybrid derived from the mutant-type DNA could be separated easily by electrophoresis, and thus the present invention has been completed. That is, the purpose of the present invention is to provide a method for detecting the mutant-type DNA, in which the hybrid of the wild-type DNA and the probe and the hybrid of the mutant-type DNA and the probe are formed, and these are separated by electrophoresis efficiently.

Means for Solving the Problems

That is, the present invention is a method for detecting the mutant-type DNA using the probe, and relates to a method for detecting the mutant-type DNA, comprising:
(1) contacting a sample containing a single-stranded DNA which has a substituted nucleotide, a deleted nucleotide region, or an inserted nucleotide region (mutant-type DNA), or/and a wild-type single-stranded DNA (wild-type DNA) corresponding thereto with the probe which hybridizes with both single-stranded DNA, to form a hybrid with the mutant-type DNA (mutant-type hybrid) or/and a hybrid with a wild-type DNA (wild-type hybrid), wherein at least one of the obtained mutant-type hybrid and wild-type hybrid has the stem structure;
(2) separating the obtained mutant-type hybrid or/and wild-type hybrid by electrophoresis on the basis of presence or absence of the stem structure or difference in the stem structure; and
(3) detecting the presence or absence of the mutant-type DNA in the sample.

Effect of the Invention

According to the method of the present invention, with respect to the DNA in which mutant-type exists, it can be easily detected whether the DNA is the mutant-type DNA or not. In particular, even when it is the mutant-type DNA which has been unable to perform separation and detection by the conventional loop hybridization method, the present invention makes it possible to isolate and detect the hybrid of the mutant-type DNA. Therefore, the methods of present invention can be applied for various tests of clinical diagnosis, such as a test for the presence or absence of cancer cells, a test for determination of appropriateness of drug effectiveness by the presence or absence of a particular gene, and the like. In addition, according to the present invention, even when it is the case where mutation occurs in codons adjacent to each other (for example, codons 12 and 13) in KRAS genetic testing, it becomes possible to detect the both mutation with high accuracy by a single measurement system.

BRIEF DESCRIPTION OF THE DRAWINGS

FIG. 12 is a table showing examples of combinations of a mutant-type hybrid and a wild-type hybrid according to the invention in the case where the mutant-type DNA has a substituted nucleotide, the probe has the nucleotide complementary to the normal nucleotide, and the hybrid has the stem structure in the probe side.

FIG. 13 is a table showing examples of combinations of a mutant-type hybrid and a wild-type hybrid according to the invention in the case where the mutant-type DNA has a substituted nucleotide, the probe has the nucleotide complementary to the substituted nucleotide, and the hybrid has the stem structure in the probe side.

FIG. 14 is a table showing examples of combinations of a mutant-type hybrid and a wild-type hybrid according to the invention in the case where the mutant-type DNA has a substituted nucleotide, the probe has the nucleotide which is complementary to the normal nucleotide, and at the time when the probe has hybridized, a hybrid which has a stem sequence in the genome side is formed.

FIG. 15 is a table showing examples of combinations of a mutant-type hybrid and a wild-type hybrid according to the invention in the case where the mutant-type DNA has a substituted nucleotide, the probe has the nucleotide which is complementary to the substituted nucleotide, and at the time when these have hybridized, a hybrid which has a stem sequence in the genome side is formed.

FIGS. 16-27 illustrate various embodiments of stem structures in accordance with the present invention.

BEST MODE FOR CARRYING OUT THE INVENTION

Figure 1:
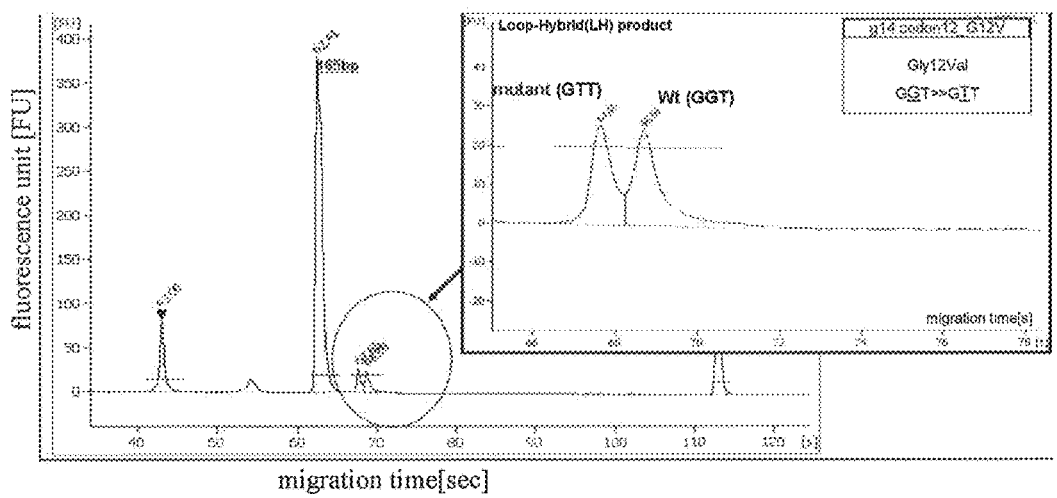
FIG. 1 is the result, obtained in Example 1, of electrophoresis carried out by microchip electrophoresis method for the hybrids of the wild-type DNA and the mutant-type DNA of KRAS gene which were prepared by the loop hybrid method (LH method) using the probe which forms the hybrid having the stem structure.

The mutant-type DNA pertaining to the present invention is the one which has the nucleotide substitution, the deleted nucleotide region, or the inserted nucleotide region (hereinafter, these are sometimes referred collectively and simply to as a mutated nucleotide region.), and any single-stranded DNA can be utilized if at least 100 to 1000 nucleotide of anteroposterior sequence of these mutated nucleotide region in the nucleotide sequence of its wild-type DNA correspond to the mutant-type DNA is known. That is, genomic DNA fragment isolated from living organisms such as animal, microorganism, bacteria, and plant, DNA fragment which can be isolated from virus, and cDNA fragment synthesized using mRNA as a template are also included. Among these mutant-type DNA, oncogene derived from human cell is included as a preferable one. In addition, the chain length (chain length as a measuring target) of mutant-type DNA which forms the hybrid is usually 50 to 2000 nucleotides preferably 100 to 500 nucleotides. It should be noted that, the above-described deleted nucleotide region represents the region in which the sequence of 1 to 200 nucleotides in the wild-type DNA is continuously missing. In addition, the above-described inserted nucleotide region represents the region in which the sequence of 1 to 200 nucleotides in the wild-type DNA is continuously inserted. It should be noted that, since the probe which hybridizes with both mutant-type DNA and wild-type DNA pertaining to the present invention may form the stem structure pertaining to the present invention by using a particular substituted nucleotide, deleted nucleotide region, or inserted nucleotide region as a target, plural substituted nucleotide, deleted nucleotide region, or inserted nucleotide region may exist other than what is used as a target.

The wild-type DNA pertaining to the present invention is the DNA which does not have mutation of the above-described mutant-type DNA pertaining to the present invention. The wild-type DNA pertaining to the present invention to be used in the methods of the present invention is the one in which the nucleotide sequence except for the mutant nucleotide region is identical to the mutant-type DNA pertaining to the present invention, and as for its length, a comparable length with the mutant-type DNA pertaining to the present invention is desirable to use, and usually it is 50 to 2000 nucleotides, preferably 100 to 500 nucleotides.

As for the above-described mutant-type DNA and the wild-type DNA pertaining to the present invention, it is preferable that the above-described DNA is purified as much as possible and unwanted substances except for nucleic acid fragment are removed. Specifically, for example, the one which is purified according to a routine method such as Boom method employing the silica carrier (Boom et al., J. Clin. Microbiol. 28:495-503 (1990)), a method employing sodium iodide solution (Proc. Natl. Acad. Sci. USA 76-2, p 615-619 (1979)) is preferable. In addition, the one which is the target DNA amplified by polymerase chain reaction (PCR reaction) well known per se, for example, by the method described in Nucleic Acids Research, 1991, Vol. 19, 3749, BioTechniques, 1994, Vol. 16, 1134-1137, may be used.

Figure 10:
FIG. 10 illustrates stem and stem-loop structures in the hybrid pertaining to the present invention.

The stem structure pertaining to the present invention is the one which is composed of single-stranded nucleotide chain which does not hybridize with the probe (does not form base pair) when it is formed in genomic DNA, and the one which is composed of single-stranded nucleotide chain which does not hybridize with the genomic DNA (does not form base pair) when it is formed in the probe, and which comprises a nucleotide sequence capable of forming base pair by itself. Said stem structure is the one which is at least 2 or more consecutive base pairs, preferably 3 or more consecutive base pairs, and it may be either consisted of the sequence capable of forming said base pair or comprising a sequence and loop sequence which are capable of forming aforementioned base pair. It should be noted that the loop sequence in the present invention is a single-stranded nucleotide chain which cannot form base pair with the probe, or a single-stranded nucleotide chain which cannot form base pair with genomic DNA, and which cannot form base pair by itself in the hybridization of genomic DNA and the probe. In addition, as for the above-described one which comprises a sequence capable of forming the base pair and loop sequence, if it is the one which contains a sequence capable of forming a base pair, the base pair may be located at any of front edge within the stem structure (most-distant position from the nucleotide sequence hybridizing with genomic DNA), the intermediate position within the stem structure (the position surrounded with the loop sequence in the stem structure), or the end within the stem structure (position nearest to the nucleotide sequence hybridizing with genomic DNA). From the point of separation performance on the electrophoresis of the mutant-type hybrid and the wild-type hybrid, among the above-described, the one which is consisted of only the sequence capable of forming base pair is preferable. It should be noted that, in the hybrid pertaining to the present invention, deduced pattern diagrams of the stem structure is shown in FIG. 10. Sequentially from the left side, a pattern diagram of the stem structure which is constituted only by a sequence capable of forming base pair; the stem structure which is constituted by a sequence capable of forming base pair and a loop sequence, and the base pair is located at the end of the stem structure; the stem structure in which the base pair is located at front edge of the stem structure; and the stem structure in which the base pair is located at the intermediate position in the stem structure, are shown, respectively. A solid line represents the stem structure, a dotted line represents a double-stranded nucleotide chain which genomic DNA and the probe form. In addition, a parallel part in the stem structure represents a sequence capable of forming base pair and an arc represents the loop sequence.

The number of above-described base pairs which may be formed is usually 2 to 20 bp, preferably 3 to 10 bp, and more preferably it is 3 to 5 bp. In addition, said base pair may comprise at least 2 consecutive base pairs, and may have multiple base pairs, and, what all are continued is preferable. The above-described stem structure may be present either in the probe side or in the genome side. If the stem structure is present in the probe side, it is more desirable than present in a genome side because the stem structure can be set up more freely by a probe design. The nucleotide chain length of the above-described stem structure is usually 4 to 60 mer, preferably 6 to 30 mer, and 6 to 20 mer is more preferable.

It should be noted that, in the present invention, the stem structure in the mutant-type hybrid and the stem structure in the wild-type hybrid will be different structure. That is, for example, if the mutant-type DNA has a substituted nucleotide, and if the probe is designed to bind with the substituted nucleotide but not to the normal nucleotide, and if the obtained hybrid has the stem structure in the probe side, its mutant-type hybrid is presumed to form the same stem structure as designed in the probe side. On the other hand, in its wild-type hybrid, it is presumed that since the probe does not bind with the normal nucleotide, the stem structure in the hybrid will comprise a nucleotide not binding with the normal nucleotide, and the stem structure in the wild-type hybrid will be longer by one nucleotide than the stem structure (designed stem structure) in the mutant-type hybrid. Thus, when the stem structure is present in the probe side, in either one of the hybrid between the mutant-type hybrid and the wild-type hybrid, the probe pertaining to the present invention provides the stem structure different from that originally designed at the time of preparation of the probe, and in consequence, the mutant-type hybrid and the wild-type hybrid can be separated efficiently. It should be noted that, like an example of the above-described wild-type hybrid, there may be a case where the stem structure in the hybrid is different from the designed one and a case where the stem structure does not form base pairs, namely the case where the hybrid does not have the stem structure, Therefore, in the present invention, if only either the mutant-type hybrid or the wild-type hybrid has the stem structure, the mutant-type hybrid and the wild-type hybrid can be separated efficiently. In addition, for example, when a mutant-type DNA has the deleted nucleotide region, and the wild-type hybrid have the stem structure in the probe side, the stem structure in the mutant-type hybrid will comprise an additional nucleotide chain of the deleted nucleotide region to the stem structure in the wild-type hybrid. In addition, for example, when a mutant-type DNA has the inserted nucleotide region, and the wild-type hybrid have the stem structure in the genome side, the stem structure in the mutant-type hybrid will comprise the additional inserted nucleotide region to the stem structure in the wild-type hybrid. As described above, in the method of the present invention, the stem structure is formed in the different structures, and this make it possible to separate the mutant-type hybrid from the wild-type hybrid efficiently by electrophoresis on the basis of difference of the stem structure.

When the stem structure pertaining to the present invention is composed of a sequence capable of forming base pair and a loop sequence, it is conceived that there may be a case where a nucleotide in the loop sequence will bind with a complementary nucleotide in the base pair. In this case, it may become impossible to form base pairs, however, even in such a case, according to the method of the present invention, since the stem structures of the mutant-type hybrid and the stem structure of the wild-type hybrid will be different structures, separation can be performed efficiently. In addition, by the use of interaction (binding) between a nucleotide in the loop sequence and a nucleotide in the base pair, even when a mutant DNA with different type of substituted nucleotide is used, different stem structure can be formed, and as a consequence, separation of mutant DNA with different type of substituted nucleotide is also possible.

Figure 11:
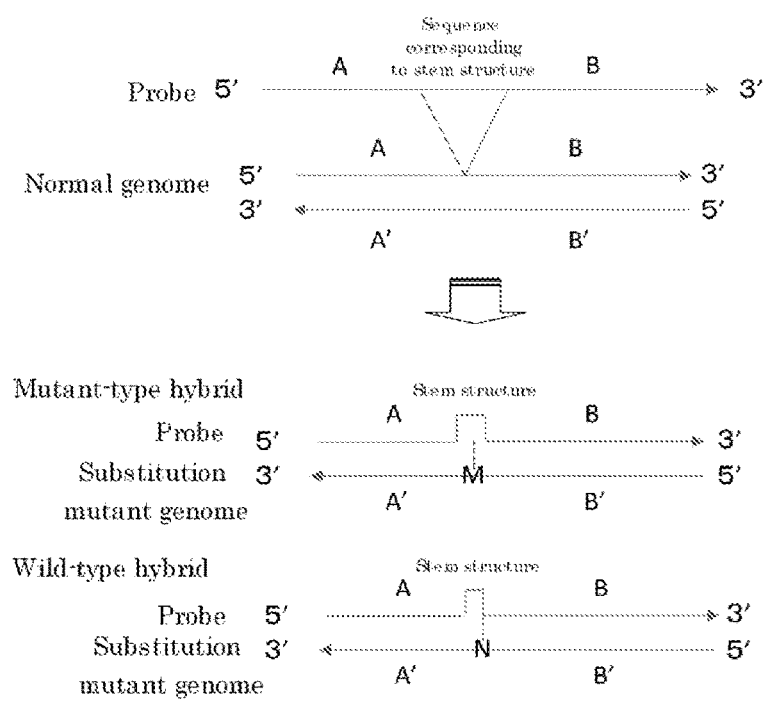
FIG. 11 illustrates a nucleotide sequence of normal (wild-type) genome having a stem sequence which is capable of forming a stem structure and inserted between portions A and B of the genome in accordance with the invention.

The probe (hereinafter, sometimes written briefly as the probe pertaining to the present invention) which hybridizes with both mutant-type DNA and wild-type DNA pertaining to the present invention is the one which hybridizes with the mutant-type DNA or the wild-type DNA, and forms respective hybrid, and on the occasion of hybridization, which makes at least one of the mutant-type hybrid and the wild-type hybrid form the above-described stem structure, and when the stem structure is formed in both hybrids, it has been designed so that the stem structure of both hybrids will be different. Such probe pertaining to the present invention is usually 30 to 300 mer, preferably 50 to 150 mer. In addition, when the stem structure is formed in the probe side, the stem structure can be set freely by designing of the probe, however, when the stem structure is formed in the genome side, the nucleotide sequence having the stem structure is retrieved from the nucleotide sequence of genome, the probe may be designed so that the stem structure is formed with that portion. Although a specific example of the probe pertaining to the present invention will be described later together with a specific example of the hybrid, for example, in the case where the DNA to be detected is a mutant-type DNA having a substituted nucleotide, and the stem structure is intended to be formed in the probe side, the probe may be designed, for example, as the scheme described below. In the case as shown in the scheme illustrated in FIG. 11, a single-stranded nucleotide sequence of normal (wild-type) genome is divided into portion A and portion B with centering on the normal nucleotide corresponding to the substituted nucleotide, and may be designed so that a sequence (corresponding sequence of the stem structure) which is capable of forming the stem structure is inserted in between portion A and portion B. It should be noted that M in the scheme represents a substituted nucleotide; N represents a normal nucleotide corresponding to the substituted nucleotide. In addition, portion A' and portion B' represent nucleotide regions complementary to the portion A and portion B, respectively.

By designing in this way, for example, when the wild-type hybrid is formed, the stem structure as designed is formed. On the other hand, in the mutant-type hybrid, since the substituted nucleotide and a nucleotide in the probe which is complementary to the normal nucleotide do not bind, it is conceived that the stem structure comprising one nucleotide complementary to the normal nucleotide is formed, and, consequently differs from wild-type stem structure. It should be noted that, as described above, when the hybrid has the stem structure in the probe side, as the sequence of the stem structure in the probe pertaining to the present invention, a nucleotide sequence which comprises, for example, a palindrome (anagram) sequence, or a nucleotide sequence containing palindrome sequence, a nucleotide sequence in which the same number of nucleotides complementary to each other are connected (for example, AAAATTTT etc.), or a nucleotide sequence containing a nucleotide sequence in which the same number of nucleotides complementary to each other are connected, are preferable.

The hybrid pertaining to the present invention is formed by hybridizing the above-described probe pertaining to the present invention with the wild-type DNA or the mutant-type DNA, however, the wild-type hybrid and the mutant-type hybrid are different in their stem structure as mentioned above. Namely, in the method of the present invention, because of forming both hybrids using the same probe, it is presumed that the number of coupled base pairs of the probe and DNA in the mutant nucleotide (region) of both hybrids differs; as a consequence, the stem structures in both hybrids differs. Therefore, it becomes possible to separate both hybrids easily by electrophoresis because this stem structure is made different.

In addition, the hybrid pertaining to the present invention may further comprise the stem structure or the loop structure, among them preferably the stem structure, in the probe side when the hybrid has the stem structure in the opposite side of nucleotide chain having the stem structure, namely, in the genomic DNA side, and in the DNA side when the hybrid has the stem structure in the probe side. By having the stem structure or the loop structure in the opposite side of the nucleotide chain which has the stem structure, higher separation performance can be achieved. Such stem structure includes the same stem structure pertaining to the present invention as described above. In addition, the loop structure is composed of a single-stranded nucleotide chain which cannot form the above-described stem structure and which does not form base pair with the probe, or a single-stranded nucleotide chain which does not form base pair with genomic DNA, and specifically, it is a single-stranded nucleotide chain which does not form base pair by itself or even if it forms base pair it is only one base pair, and does not form base pair with the probe, or a single-stranded nucleotide chain which does not form base pair with genomic DNA. The chain length thereof etc. may be the one according to the stem structure.

The above-described probe as well as the above-described hybrid may be designed appropriately and synthesized depending on the kind (the single-stranded DNA having the above-described substituted nucleotide, deleted nucleotide region, or inserted nucleotide region) of mutant-type DNA to be a target of measurement, or on whether it hybridizes with the mutant nucleotide region or a normal nucleotide or a normal nucleotide region corresponding to the mutant nucleotide region, however, as for the specific example of the probe, it will be described by dividing into cases as follows.

(I) In the case where DNA is the mutant-type DNA having a substituted nucleotide
  (I-1) In the case where the hybrid which has the stem structure in the probe side is formed
    (a) In the case where the probe binds with a normal nucleotide
    (b) In the case where the probe binds with a substituted nucleotide
  (I-2) In the case where the hybrid which has the stem structure in the genome side is formed
    (a) In the case where the probe binds with a normal nucleotide
    (b) In the case where probe binds with a substituted nucleotide
(II) In the case where DNA is the mutant-type DNA which has the deleted nucleotide region
  (II-1) In the case where the hybrid which has the stem structure in the probe side is formed
    (a) In the case where at least the mutant-type hybrid forms the stem structure
    (b) In the case where at least the wild-type hybrid forms the stem structure (II-2) In the case where the hybrid which has the stem structure in the genome side is formed
(III) In the case where DNA is a mutant-type DNA which has the inserted nucleotide region
  (III-1) In the case where the hybrid which has the stem structure in the genome side is formed
    (a) In the case where at least the mutant-type hybrid forms the stem structure
    (b) In the case where at least the wild-type hybrid forms the stem structure
  (III-2) In the case where DNA has the stem structure in the probe side
    (a) In the case where at least the wild-type hybrid forms the stem structure
    (b) In the case where at least the mutant-type hybrid forms the stem structure
(IV) In the case where the stem structure or the loop structure is further formed in the chain opposite to the nucleotide chain which has the stem structure

[Specific Example of the Probe and the Hybrid Pertaining to the Present Invention]

(I) In the Case where DNA is a Mutant-Type DNA which has a Substituted Nucleotide
(I-1) In the Case where the Hybrid which has the Stem Structure in the Probe Side is Formed In the case where a mutant-type DNA is the one which has a substituted nucleotide, and at the time when the probe has hybridized, the hybrid which has the stem structure in the probe side is formed, for example, the probe pertaining to the present invention to be used has the following structure.

$$3'\ 1stSS_1-X'_1-St_{P1}-X'_2-X'_3-X'_4-X'_5-2ndSS_1\ 5',$$
or
$$3'\ 1stSS_1-X'_1-X'_2-X'_3-X'_4-St_{P1}-X'_5-2ndSS_1\ 5'$$

[In said nucleotide sequences, $1stSS_1$ and $2ndSS_1$ represent the single-stranded nucleotide sequence which is complementary to the wild-type DNA and the mutant-type DNA, respectively; $X'_1$ and $X'_5$ represent arbitrary nucleotide, respectively; and $X'_2$ to $X'_4$ represent a nucleotide or a bond, and either one of them is the nucleotide complementary to the mutant nucleotide or the nucleotide complementary to a normal nucleotide which corresponds to the mutant nucleotide; the nucleotide complementary to said mutant nucleotide or the nucleotide complementary to the normal nucleotide is located in the position corresponding to the substituted nucleotide in the mutant-type DNA or the normal nucleotide in the wild-type DNA when hybridized. $St_{P1}$ represents the sequence which forms the stem structure in the probe side (hereinafter, written briefly as the probe side stem sequence).].

The arbitrary nucleotide in the above-described $X'_1$ and $X'_5$ is any nucleotide consisted of adenine, guanine, thymine, or cytosine. Hereinafter, the arbitrary nucleotide in the present invention refers to the same one.

The bond in $X'_2$ to $X'_4$ represents the case where the nucleotide is not represented but it combines the nucleotides on both adjacent sides. For example, when $X'_2$ is adenine (A), $X'_3$ is the bond and $X'_4$ is guanine (G), $X'_2$-$X'_3$-$X'_4$ represents A-G. Hereinafter, the bond in the present invention refers to the same one.

The probe side stem sequence pertaining to the present invention is the one which does not hybridize (does not form base pairs) with genomic DNA on the occasion of forming the hybrid, and the sequence in which the single-stranded nucleotide chain in the probe is capable of forming base pairs by itself, and is capable of forming the above-described stem structure. Although said probe side stem sequence becomes the stem structure by itself, it may form the stem structure by coupling with a nucleotide or a nucleotide sequence adjacent to the stem sequence which does not form base pair with genomic DNA. In this case, since the constitution of the stem sequence is altered, there may be a situation that the above-described base pairs cannot be formed, consequently, the stem structure pertaining to the present invention cannot be constituted (but forms the loop structure), Therefore, it is necessary to design so that at least any one of the mutant-type hybrid and the wild-type hybrid has the stem structure pertaining to the present invention.

The probe side stem sequence pertaining to the present invention is the one which usually consists of 4 to 60 mer, preferably 6 to 20 mer. In addition, the base pair in the stem structure at the time when said probe side stem sequence forms the stem structure includes the one which consists of a consecutive double-stranded base pair of usually 2 to 20 bp, preferably 3 to 10 bp and more preferably 3 to 5 bp, or the one which comprises a consecutive double-stranded base pair of usually 2 to 20 bp, preferably 3 to 10 bp and more preferably 3 to 5 bp and a loop sequence. Among them, the one which consists of a consecutive double-stranded base pair is preferable.

When the above-described probe is hybridized with mutant-type DNA, the following mutant-type hybrid is formed.

Mutant-Type Hybrid $$Probe:\quad 3'\ 1stSS_1-X'_1-St_{P1}-X'_2-X'_3-X'_4-X'_5-2ndSS_1\ 5'$$
$$Genome:\quad 5'\ 1stDS_1-X_1-X_2-X_3-X_4-X_5-2ndDS_1\ 3'$$
or
$$Probe:\quad 3'\ 1stSS_1-X'_1-X'_2-X'_3-X'_4-St_{P1}-X'_5-2ndSS_1\ 5'$$
$$Genome:\quad 5'\ 1stDS_1-X_1-X_2-X_3-X_4-X_5-2ndDS_1\ 3'$$

(In said hybrid, $1stSS_1$ and $2ndSS_1$ are the same as described above, and $1stDS_1$ and $2ndDS_1$ represent nucleotide sequence region which forms complementary double strand with $1stSS_1$ and $2ndSS_1$, respectively; although $X'_1$ to $X'_5$ are the same as described above, $X_1$ and $X_5$ represent nucleotide, $X'_1$ and $X_1$, and $X'_5$ and $X_5$ are complementary nucleotides, respectively, and $X_2$ to $X_4$ represent the nucleotide or the bond, and any one of them is the substituted nucleotide, and it is the nucleotide or the bond complementary to the corresponding $X'_2$ to $X'_4$. In this regard, however, when any of $X'_2$ to $X'_4$ in the probe is the nucleotide complementary to the normal nucleotide, it will not be complementary to the substituted nucleotide of any of corresponding $X_2$ to $X_4$.).

In addition, when the above-described probe is hybridized with the wild-type DNA, the following mutant-type hybrid is formed.

Wild-Type Hybrid $$Probe:\quad 3'\ 1stSS_1-X'_1-St_{P1}-X'_2-X'_3-X'_4-X'_5-2ndSS_1\ 5'$$
$$Genome:\quad 5'\ 1stDS_1-X_1-Y_2-Y_3-Y_4-X_5-2ndDS_1\ 3'$$
or
$$Probe:\quad 3'\ 1stSS_1-X'_1-X'_2-X'_3-X'_4-St_{P1}-X'_5-2ndSS_1\ 5'$$
$$Genome:\quad 5'\ 1stDS_1-X_1-Y_2-Y_3-Y_4-X_5-2ndDS_1\ 3'$$

(In said hybrid, although $1stSS_1$, $2ndSS_1$ $1stDS_1$, $2ndDS_1$, $X'_1$ to $X'_5$, and $X_1$ and $X_5$ are the same as described above, $X'_1$ and $X_1$, and $X'_5$ and $X_5$ are complementary nucleotides, respectively; $Y_2$ to $Y_4$ represent the nucleotide or the bond, and any one of them is a normal nucleotide corresponding to mutant nucleotide, and it is the nucleotide or the bond complementary to corresponding $X'_2$ to $X'_4$. In this regard, however, when any one of $X'_2$ to $X'_4$ in the probe is the nucleotide complementary to a substituted nucleotide, it will not be complementary to the normal nucleotide of any one of corresponding $Y_2$ to $Y_4$.).

The case where the mutant-type DNA has a substituted nucleotide and has the stem structure in the probe side will be explained as follows by further dividing the case into (a) a case where the probe has the nucleotide complementary to a normal nucleotide and (b) a case where the probe has the nucleotide complementary to a substituted nucleotide.

(I-1) (a) in the Case where the Hybrid which has the Stem Structure in the Probe Side is Formed, and the Probe Binds with a Normal Nucleotide In the case where the mutant-type DNA is a DNA which has a substituted nucleotide, and at the time when the probe has hybridized, the probe binds with normal nucleotide and forms the hybrid which has the stem structure in the probe side, said probe pertaining to the present invention to be used has, for example, the following structure.

```
3' 1stSS₁₁-X'₁₁-St_P11-X'₁₂-X'₁₃-X'₁₄-X'₁₅-2ndSS₁₁ 5'
or
3' 1stSS₁₁-X'₁₁-X'₁₂-X'₁₃-X'₁₄-St_P11-X'₁₅-2ndSS₁₁ 5'
```

(In said nucleotide sequence, $1stSS_{11}$ and $2ndSS_{11}$ represent a single-stranded nucleotide sequence which is complementary to the wild-type DNA and the mutant-type DNA, respectively; $X'_{11}$ and $X'_{15}$ represent each arbitrary nucleotide; and $X'_{12}$ to $X'_{14}$ represent the nucleotide or the bond, and either one of them is the nucleotide complementary to the normal nucleotide which corresponds to the mutant nucleotide, and at the time when it has hybridized, said nucleotide complementary to the normal nucleotide is located in the position corresponding to the substituted nucleotide of the mutant-type DNA or the normal nucleotide of the wild-type DNA. $St_{P11}$ represents the probe side stem sequence.).

When said probe is hybridized with the mutant-type DNA, the following mutant-type hybrid is formed.

Mutant-Type Hybrid

```
Probe:
3' 1stSS₁₁-X'₁₁-X'₁₂-X'₁₃-X'₁₄-St_P11-X'₁₅-2ndSS₁₁ 5'

Genome:
5' 1stDS₁₁-X₁₁-X₁₂-X₁₃-X₁₄-X₁₅-2ndDS₁₁ 3'
or

Probe:
3' 1stSS₁₁-X'₁₁-St_P11-X'₁₂-X'₁₃-X'₁₄-X'₁₅-2ndSS₁₁ 5'

Genome:
5' 1stDS₁₁-X₁₁-X₁₂-X₁₃-X₁₄-X₁₅-2ndDS₁₁ 3'
```

(In said hybrid, $X'_{11}$ to $X'_{15}$, $St_{P11}$ are the same as described above; $1stSS_{11}$, $2ndSS_{11}$ are the same as described above, and $1stDS_1$ and $2ndDS_{11}$ represent the nucleotide sequence region which forms complementary double strand with $1stSS_{11}$ and $2ndSS_{11}$, respectively; $X_{11}$ and $X_{15}$ represent nucleotide; $X'_{11}$ and $X_{11}$, and $X'_{15}$ and $X_{15}$ are complementary nucleotides; $X_{12}$ to $X_{14}$ represent the nucleotide or the bond, and either one of them is the substituted nucleotide; the substituted nucleotide in the $X_{12}$ to $X_{14}$ cannot be the nucleotide complementary to the corresponding $X'_{12}$ to $X'_{14}$, however, the rest are the nucleotide or the bond complementary to the corresponding $X'_{12}$ to $X'_{14}$.)

It should be noted that, since any one of $X'_{12}$ to $X'_{14}$ in the above-described mutant-type hybrid is the nucleotide complementary to the normal nucleotide, it does not form a base pair with substituted nucleotide in the $X_{12}$ to $X_{14}$. Therefore, when the nucleotide is present in between the probe side stem sequence and the nucleotide complementary to the normal nucleotide, even if the nucleotide is the nucleotide complementary to the genome side nucleotide, its binding will be unstable, and hence unable to form the base pair. In consequence, in some instances, $X'_{12}$ to $X'_{14}$ also become unable to form base pairs, and such nucleotide which is unable to form base pair is coupled to the stem sequence. It should be noted that, in this case, these nucleotides may form the stem structure depending on the combination of nucleotides which have become unable to form stem sequence and base pair, or otherwise may form a simple loop structure. For example, as a scheme described below, when $X_{13}$ is substituted nucleotide (in the scheme, represented by M), and $X'_{13}$ is the nucleotide (in the scheme, represented by N') complementary to normal nucleotide, in normal circumstances, $X_{12}$ and $X'_{12}$ form a base pair, however, since nucleotides in adjacent both sides do not form base pairs with nucleotides in genome side, the entire $St_{P11}$-$X'_{12}$-N' ($X'_{13}$) does not form base pair with the genome side of mutant-type DNA, and eventually the stem structure is formed by these.

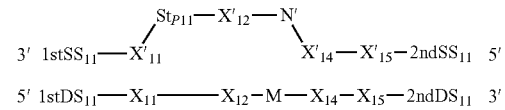

In addition, if the above-described probe is hybridized with the wild-type DNA, the following wild-type hybrid is formed.

Wild-Type Hybrid

```
Probe:
3' 1stSS₁₁-X'₁₁-St_P11-X'₁₂-X'₁₃-X'₁₄-X'₁₅-2ndSS₁₁ 5'

Genome:
5' 1stDS₁₁-X₁₁-Y₁₂-Y₁₃-Y₁₄-X₁₅-2ndDS₁₁ 3'
or

Probe:
3' 1stSS₁₁-X'₁₁-X'₁₂-X'₁₃-X'₁₄-St_P11-X'₁₅-2ndSS₁₁ 5'

Genome:
5' 1stDS₁₁-X₁₁-Y₁₂-Y₁₃-Y₁₄-X₁₅-2ndDS₁₁ 3'
```

(In said hybrid, $1stSS_{11}$, $2ndSS_{11}$ are same as described above, and $1stDS_{11}$, $2ndDS_{11}$, $X'_{11}$ to $X'_{15}$, $X_{11}$, $X_{15}$ and $St_{P11}$ are also the same as described above; however, $X_{11}$ and $X_{15}$ are the nucleotides complementary to $X'_{11}$ and $X'_{15}$, respectively; and $Y_{12}$ to $Y_{14}$ represent the nucleotide or the bond, and any one of them is the normal nucleotide corresponding to the mutant nucleotide, and it is the nucleotide or the bond complementary to the corresponding to $X'_{12}$ to $X'_{14}$.).

In the above-described wild-type hybrid, the stem structure is formed only by a stem sequence which is designed in the probe. In the method for detecting mutant-type DNA of the present invention, since said wild-type hybrid will have at least the stem structure, the above-described mutant-type hybrid may not have stem structure. It should be noted that, even when the above-described mutant-type hybrid has the stem structure, it will have the stem structure different from said wild-type hybrid.

In the case where the above-described mutant-type DNA is the one which has a substituted nucleotide, and the probe has the nucleotide complementary to the normal nucleotide, and the hybrid having the stem structure in the probe side is formed, the specific example of combination of the mutant-type hybrid and the wild-type hybrid includes, for example, the combinations as listed in the table shown in FIG. 12.

In the table shown in FIG. 12, 1stSS and 2ndSS represent the single-stranded nucleotide sequence which is complementary to the wild-type DNA and the mutant-type DNA, respectively; 1stDS and 2ndDS represent the nucleotide sequence regions which form complementary double strand with 1stSS and 2ndSS, respectively; X represents the nucleotide which becomes complementary between the probe and the genomic DNA; M represents the substituted nucleotide, N represents the normal nucleotide corresponding to the substituted nucleotide, and N' represents the nucleotide complementary to the normal nucleotide, and St represents the probe side stem sequence. In addition, the area enclosed with square (□) represents that it does not form base pair with genomic DNA, but forms the stem structure or the loop structure.

(I-1) (b) In the Case where the Hybrid which has the Stem Structure in the Probe Side is Formed, and the Probe Binds with a Substituted Nucleotide In the case where the mutant-type DNA is the one which has a substituted nucleotide, and at the time when the probe has hybridized, the probe binds with substituted nucleotide and forms the hybrid which has the stem structure in the probe side, said probe pertaining to the present invention to be used has, for example, the following structure.

```
3' 1stSS_{21}-X'_{21}-St_{P21}-X'_{22}-X'_{23}-X'_{24}-X'_{25}-2ndSS_{21} 5'
or
3' 1stSS_{21}-X'_{21}-X'_{22}-X'_{23}-X'_{24}-St_{P21}-X'_{25}-2ndSS_{21} 5'
```

(In said nucleotide sequence, $1stSS_{21}$ and $2ndSS_{21}$ represent the single-stranded nucleotide sequence which is complementary to the wild-type DNA and the mutant-type DNA, respectively; $X'_{21}$ and $X'_{25}$ represent arbitrary nucleotide; and $X'_{22}$ to $X'_{24}$ represent the nucleotide or the bond, and any one of them is the nucleotide complementary to the substituted nucleotide, and at the time when it has hybridized, said nucleotide complementary to the substituted nucleotide is located in the position corresponding to the substituted nucleotide of the mutant-type DNA or the normal nucleotide of the wild-type DNA. $St_{P21}$ represents the probe side stem sequence.).

When said probe is hybridized with the mutant-type DNA, the following mutant-type hybrid is formed.

Mutant-Type Hybrid

```
Probe:
3' 1stSS_{21}-X'_{21}-St_{P21}-X'_{22}-X'_{23}-X'_{24}-X'_{25}-2ndSS_{21} 5'

Genome:
5' 1stDS_{21}-X_{21}-X_{22}-X_{23}-X_{24}-X_{25}-2ndSS_{21} 3'
or

Probe:
3' 1stSS_{21}-X'_{21}-X'_{22}-X'_{23}-X'_{24}-St_{P21}-X'_{25}-2ndSS_{21} 5'

Genome:
5' 1stDS_{21}-X_{21}-X_{22}-X_{23}-X_{24}-X_{25}-2ndDS_{21} 3'
```

(In said hybrid, $1stSS_{21}$, $2ndSS_{21}$, $X'_{21}$ to $X'_{25}$, and $St_{P11}$ are the same as described above, and $1stDS_{21}$ and $2ndDS_{21}$ represent the nucleotide sequence region which forms complementary double strand with $1stSS_{21}$, $2ndSS_{21}$, respectively; $X_{21}$ and $X_{25}$ represent nucleotide; $X'_{21}$ and $X_{21}$, and $X'_{25}$ and $X_{25}$ represent complementary nucleotides; and $X_{22}$ to $X_{24}$ represent the nucleotide or the bond, and any one of them is the substituted nucleotide, and it is the nucleotide or the bond complementary to the corresponding to $X'_{22}$ to $X'_{24}$.).

In said mutant-type hybrid, the stem structure is formed only by the stem sequence which is designed by the probe. In the method for detecting mutant-type DNA of the present invention, since said mutant-type hybrid will have at least the stem structure, the wild-type hybrid described below may not have stem structure. It should be noted that, even when the wild-type hybrid described below has the stem structure; it will have the stem structure different from said mutant-type hybrid.

In addition, if the above-described probe is hybridized with the wild-type DNA, the following wild-type hybrid is formed.

Wild-Type Hybrid

```
Probe:
3' 1stSS_{21}-X'_{21}-St_{P21}-X'_{22}-X'_{23}-X'_{24}-X'_{25}-2ndSS_{21} 5'

Genome:
5' 1stDS_{21}-X_{21}-Y_{22}-Y_{23}-Y_{24}-X_{25}-2ndSS_{21} 3'
or

Probe:
3' 1stSS_{21}-X'_{21}-X'_{22}-X'_{23}-X'_{24}-St_{P21}-X'_{25}-2ndSS_{21} 5'

Genome:
5' 1stDS_{21}-X_{21}-Y_{22}-Y_{23}-Y_{24}-X_{25}-2ndDS_{21} 3'
```

(In said hybrid, $1stSS_{21}$, $2ndSS_{21}$, $1stDS_{21}$, $2ndDS_{21}$, $X'_{21}$ to $X'_{25}$, $X_{21}$, $X_{25}$ and $St_{P21}$ are the same as described above; however $X_{21}$ and $X_{25}$ are the nucleotides complementary to $X'_{21}$ and $X'_{25}$, respectively; $Y_{22}$ to $Y_{24}$ represent the nucleotide or the bond, and any one of them is the normal nucleotide corresponding to a mutant nucleotide, and the rest of $Y_{22}$ to $Y_{24}$ is the bond or the nucleotide complementary to the corresponding to $Y'_{22}$ to $Y'_{24}$.).

It should be noted that, since any one of $X'_{22}$ to $X'_{24}$ in the above-described wild-type hybrid is the nucleotide complementary to the substituted nucleotide, it does not form the base pair with any one of normal nucleotide in the $Y_{22}$ to $Y_{24}$. In consequence, in some instances, $X'_{22}$ to $X'_{24}$ are unable to form the base pair due to the effect of structure of the stem sequence, and such nucleotide which is unable to form the base pair is coupled to the probe side stem sequence. It should be noted that, in this case, these nucleotides may form the stem structure depending on the combination of nucleotides which have become unable to form stem sequence and base pair, or otherwise may form the loop structure simply.

In the case where the above-described mutant-type DNA is the one which has the substituted nucleotide, and the probe has the nucleotide complementary to the substituted nucleotide, and it forms the hybrid having the stem sequence in the probe side, the specific example of combination of the mutant-type hybrid and the wild-type hybrid includes, for example, the combinations as listed in the table shown in FIG. 13.

In the table shown in FIG. 13, 1stSS and 2ndSS represent the single-stranded nucleotide sequence which is complementary to the wild-type DNA and the mutant-type DNA, respectively; 1stDS and 2ndDS represent the nucleotide sequence regions which form complementary double strand with 1stSS and 2ndSS, respectively; X represents the nucleotide which becomes complementary each other between the probe and genomic DNA; M represents a substituted nucleotide, N represents a normal nucleotide corresponding to the substituted nucleotide, and M' represents the nucleotide complementary to a substituted nucleotide, and St represents the probe side stem sequence. In addition, the area enclosed with square (□) represents that it does not form base pair with genomic DNA, but forms the stem structure or the loop structure.

As mentioned above, in the case where the mutant-type DNA is the DNA which has a substituted nucleotide, and the hybrid which has the stem structure in the probe side is formed, the hybrid further comprises the one which forms a further the stem structure or the loop structure in the genome side. The details will be described in (IV).

(I-2) In the Case where the Hybrid which has the Stem Structure in the Genome Side is Formed In the case where a mutant-type DNA is the one which has a substituted nucleotide, and at the time when the probe has hybridized, it forms the hybrid which has the stem structure in the genome side, the probe pertaining to the present invention to be used has, for example, the following structure.

$$3'\ 1stSS_{311}\text{-}X'_{311}\text{-}X'_{312}\text{-}2ndSS_{311}\ 5'$$

($1stSS_{31}$ and $2ndSS_{31}$ represent the single-stranded nucleotide sequence which is complementary to the wild-type DNA and the mutant-type DNA, respectively; $X'_{31}$, $X'_{32}$, and $X'_{33}$ represent arbitrary nucleotide respectively; and $X'_{32}$ represent the nucleotide which is complementary to the substituted nucleotide or the nucleotide complementary to the normal nucleotide.)

When said probe is hybridized with the mutant-type DNA, the following mutant-type hybrid is formed.

Mutant-Type Hybrid

| Probe: | 3' $1stSS_{31}$-$X'_{31}$-$X'_{32}$-$X'_{33}$-$2ndSS_{31}$ 5' |
|---|---|
| Genome: | 5' $1stDS_{31}$-$X_{31}$-$M_{32}$-$St_{G31}$-$X_{33}$-$2ndDS_{31}$ 3' |
| or | |
| Probe: | 3' $1stSS_{31}$-$X'_{31}$-$X'_{32}$-$X'_{33}$-$2ndSS_{31}$ 5' |
| Genome: | 5' $1stDS_{31}$-$X_{31}$-$St_{G31}$-$M_{31}$-$X_{33}$-$2ndDS_{31}$ 3' | or (In said hybrid, $1stSS_{31}$, $2ndSS_{31}$, $X'_{31}$ to $X'_{33}$ are the same as described above. $1stDS_{31}$, $2ndDS_{31}$ represent the nucleotide sequence region which forms complementary double strand together with $1stSS_{31}$, $2ndSS_{31}$, respectively; $X_{31}$ and $X_{33}$ each represent nucleotide, which are nucleotides complementary to $X'_{31}$ and $X'_{33}$, respectively; $M_{31}$ represents substituted nucleotide; $St_{G31}$ represents a sequence (hereinafter, sometimes abbreviated as genome side stem sequence) which forms the stem structure in the genome side.

In said hybrid, when $X'_{32}$ is the nucleotide which is complementary to the substituted nucleotide, the genome side stem sequence forms the stem structure; and when $X'_{32}$ is the nucleotide which is complementary to the normal nucleotide, the genome side stem sequence and the substituted nucleotide are coupled to form the stem structure or the loop structure.

Similarly as the case of the above-described probe side stem sequence, the above-described genome side stem sequence is the sequence which does not hybridize (does not form base pair) with the probe at the time when the hybrid is formed, and the sequence which the single-stranded nucleotide chain in the genome forms the base pairs by itself, and the one which forms the above-described stem structure. Although said stem sequence becomes the stem structure by itself, when $X'_{32}$ is the nucleotide complementary to the normal nucleotide, the stem structure or the loop structure is formed with $St_{G31}$-$M_{31}$. It should be noted that, when the loop structure is formed, it is necessary to design so that the wild-type hybrid has the stem structure pertaining to the present invention.

The genome side stem sequence usually consists of 6 to 60 mer, preferably 6 to 10 mer, and the base pair in the stem structure at the time when said genome side stem sequence forms the stem structure includes the one which consists of a consecutive double-stranded base pairs of usually 2 to 20 bp, preferably 3 to 5 bp, or the loop structure which has the consecutive double-stranded base pairs of usually 3 to 20 bp, preferably 3 to 5 bp. Among them, the one which consists of a consecutive double-stranded base pairs of 3 to 20 bp, preferably 3 to 5 bp is preferable.

When the above-described probe is hybridized with the wild-type DNA, the following mutant-type hybrid is formed.

Wild-Type Hybrid

| Probe: | 3' $1stSS_{31}$-$X'_{31}$-$X'_{32}$-$X'_{33}$-$2ndSS_{31}$ 5' |
|---|---|
| Genome: | 5' $1stDS_{31}$-$X_{31}$-$St_{G31}$-$N_{31}$-$X_{33}$-$2ndDS_{31}$ 3' |
| or | |
| Probe: | 3' $1stSS_{31}$-$X'_{31}$-$X'_{32}$-$X'_{33}$-$2ndSS_{31}$ 5' |
| Genome: | 5' $1stDS_{31}$-$X_{31}$-$N_{31}$-$St_{G31}$-$X_{33}$-$2ndDS_{31}$ 3' |

($1stSS_{31}$, $2ndSS_{31}$, $1stDS_{31}$, $2ndDS_{31}$, $X'_{31}$ to $X'_{33}$, $X_{31}$, $X_{33}$, and $St_{G31}$ are the same as described above. $N_{31}$ represents the normal nucleotide corresponding to the substituted nucleotide.).

In said hybrid, when $X'_{32}$ is the nucleotide complementary to the normal nucleotide, the genome side stem sequence forms the stem structure; and when $X'_{32}$ is the nucleotide complementary to the substituted nucleotide, the genome side stem sequence and the substituted nucleotide are coupled to form the stem structure or the loop structure.

(I-2) (a) In the Case where the Hybrid which has the Stem Structure in the Genome Side is Formed, and the Probe Binds with a Normal Nucleotide In the case where the mutant-type DNA is the one which has a substituted nucleotide, and at the time when the probe has hybridized, the probe binds with a normal nucleotide and form the hybrid which has the stem structure in the genome side, the probe pertaining to the present invention to be used has, for example, the following structure.

$$3'\ 1stSS_{41}\text{-}X'_{41}\text{-}N'_{41}\text{-}X'_{43}\text{-}2ndSS_{41}\ 5'$$

($1stSS_{41}$, $2ndSS_{41}$ represent the single-stranded nucleotide sequence which is complementary to the wild-type DNA and the mutant-type DNA, respectively; $X'_{41}$ and $X'_{43}$ represent the nucleotides, respectively; $N'_{41}$ represents the nucleotide complementary to the normal nucleotide.)

When said probe is hybridized with the mutant-type DNA, the following mutant-type hybrid is formed.

Mutant-Type Hybrid

```
Probe:    3' 1stSS₄₁-X'₄₁-N'₄₁-X'₄₃-2ndSS₄₁ 5'
Genome:   5' 1stDS₄₁-X₄₁-M₄₁-St_G41-X₄₃-2ndSS₄₁ 3'
or
Probe:    3' 1stSS₄₁-X'₄₁-N'₄₁-X'₄₃-2ndSS₄₁ 5'
Genome:   5' 1stDS₄₁-X₄₁-St_G41-M₄₁-X₄₃-2ndSS₄₁ 3'
```

(In said hybrid, $1stSS_{41}$, $2ndSS_{41}$, $X'_{41}$, $X'_{43}$, and $N'_{41}$ are the same as described above. $1stDS_{41}$ and $2ndDS_{41}$ represent the nucleotide sequence region which forms complementary double strand with $1stSS_{41}$ and $2ndSS_{41}$, respectively; $X_{41}$ and $X_{43}$ represent nucleotide, and these are the nucleotides complementary to $X'_{41}$ and $X'_{43}$, respectively; $M_{41}$ represents the substituted nucleotide; and $St_{G41}$ represents the genome side stem sequence.)

In the above-described hybrid, since the substituted nucleotide $M_{41}$ cannot form base pairs with $N'_{41}$, the stem structure or the loop structure is formed by coupling with $St_{G41}$.

When the above-described probe is hybridized with the wild-type DNA, the following wild-type hybrid is formed.

Wild-Type Hybrid

```
Probe:    3' 1stSS₄₁-X'₄₁-N'₄₁-X₄₃-2ndSS₄₁ 5'
Genome:   5' 1stDS₄₁-X₄₁-St_G41-N₄₁-X₄₃-2ndS₄₁ 3'
or
Probe:    3' 1stSS₄₁-X'₄₁-X'₄₂-X'₄₃-2ndSS₄₁ 5'
Genome:   5' 1stDS₄₁-X₄₁-N₄₁-St_G41-X₄₃-2ndDS₃₁ 3'
```

($1stSS_{41}$, $2ndSS_{41}$, $1stDS_{41}$, $2ndDS_{41}$, $X'_{41}$, $X'_{42}$ and $X'_{43}$, $X_{41}$, $X_{43}$, and $St_{G41}$ are the same as described above. $N_{41}$ represents the normal nucleotide corresponding to the substituted nucleotide.)

In said hybrid, the genome side stem sequence forms the stem structure.

In the case where the mutant-type DNA is the one which has a substituted nucleotide, and at the time when the probe has hybridized, the hybrid which has a stem sequence in the genome side is formed; the specific example of combination of the mutant-type hybrid and the wild-type hybrid includes, for example, the combinations as listed in the table shown in FIG. 14.

In the table shown in FIG. 14, 1stSS, 2ndSS represent the single-stranded nucleotide sequence which is complementary to the wild-type DNA and mutant-type DNA, respectively; 1stDS, 2ndDS represent the nucleotide sequence regions which form complementary double strand with 1stSS, 2ndSS, respectively; X represents the nucleotide which becomes complementary between the probe and genomic DNA; M represents the substituted nucleotide, N represents the normal nucleotide corresponding to the substituted nucleotide, and N' represents the nucleotide complementary to the normal nucleotide, and (St) represents the genome side stem sequence. In addition, the area enclosed with square (□) represents that it does not form base pair with the probe, but forms the stem structure or the loop structure.

(I-2) (b) In the Case where the Hybrid which has the Stem Structure in the Genome Side is Formed, and the Probe Binds with a Substituted Nucleotide In the case where the mutant-type DNA is the one which has a substituted nucleotide, and at the time when the probe has hybridized, the probe binds with substituted nucleotide and forms the hybrid which has the stem structure in the genome side, the probe pertaining to the present invention to be used has, for example, the following structure.

```
3' 1stSS₃₂₁-X'₃₂₁-X'₃₂₂-2ndSS₃₂₁ 5'
```

($1stSS_{31}$, $2ndSS_{51}$ represent the single-stranded nucleotide sequence which is complementary to the wild-type DNA and the mutant-type DNA, respectively; $X'_{51}$ and $X'_{53}$ represent the nucleotides, respectively; $M'_{51}$ represents the nucleotide complementary to the substituted nucleotide.)

When said probe is hybridized with the mutant-type DNA, the following mutant-type hybrid is formed.

Mutant-Type Hybrid

```
Probe:    3' 1stSS₅₁-X'₅₁-M'₅₁-X'₅₃-2ndSS₅₁ 5'
Genome:   5' 1stDS₅₁-X₅₁-M₅₁-St_G51-X₅₃-2ndDS₅₁ 3'
or
Probe:    3' 1stSS₅₁-X'₅₁-M'₅₁-X'₅₃-2ndSS₅₁ 5'
Genome:   5' 1stDS₅₁-X₅₁-St_G51-M₅₁-X₅₃-2ndDS₅₁ 3'
```

(In said hybrid, $1stSS_{51}$, $2ndSS_{51}$, $X'_{51}$, $X'_{53}$, and $M'_{51}$ are the same as described above. $1stDS_{51}$, $2ndDS_{51}$ represent the nucleotide sequence regions which form base pairs with $1stSS_{51}$ and $2ndSS_{51}$, respectively; $X_{51}$ and $X_{53}$ represent nucleotide, and $X'_{51}$ and $X_{51}$, and $X'_{53}$ and $X_{53}$ are complementary nucleotides, respectively; $M_{51}$ represents the substituted nucleotide; and $St_{G41}$ represents the genome side stem sequence.)

In said hybrid, the genome side stem sequence forms the stem structure.

When the above-described probe is hybridized with the wild-type DNA, the following wild-type hybrid is formed.

Wild-Type Hybrid

```
Probe:    3' 1stSS₅₁-X'₅₁-M'₅₁-X'₅₃-2ndSS₅₁ 5'
Genome:   5' 1stDS₅₁-X₅₁-St_G51-N₅₁-X₅₃-2ndDS₅₁ 3'
or
Probe:    3' 1stSS₅₁-X'₅₁-M'₅₁-X'₅₃-2ndSS₅₁ 5'
Genome:   5' 1stDS₅₁-X₅₁-N₅₁-St_G51-X₅₃-2ndDS₅₁ 3'
```

(In said hybrid, $1stSS_{51}$, $2ndSS_{51}$, $1stDS_{51}$, $2ndDS_{51}$, $X'_{51}$ to $X'_{53}$ are the same as described above. $X_{51}$ and $X_{53}$ represent the nucleotides, respectively, and these are nucleotides complementary to $X'_{51}$ and $X'_{53}$, respectively; $N_{51}$ represents the normal nucleotide corresponding to the substituted nucleotide; and $St_{G51}$ represents the genome side stem sequence.)

In the above-described hybrid, since $N_{51}$ cannot form base pairs with $M'_{51}$, the stem structure or the loop structure is formed by coupling with $St_{G51}$.

In the case where the mutant-type DNA is the one which has a substituted nucleotide, and the probe has the nucleotide which is complementary to the substituted nucleotide, and at the time when these have hybridized, the hybrid which has a stem sequence in the genome side is formed; the specific example of combination of the mutant-type hybrid and the wild-type hybrid includes, for example, the combinations as listed in the table shown in FIG. 15.

In the table shown in FIG. 15, 1stSS, 2ndSS represent the single-stranded nucleotide sequence which is complementary to the wild-type DNA and mutant-type DNA, respectively; 1stDS, 2ndDS represent the nucleotide sequence regions which form complementary double strand with 1stSS, 2ndSS, respectively; X represents the nucleotide which is complementary each other between the probe and genomic DNA; M represents a substituted nucleotide, N represents a normal nucleotide corresponding to the substituted nucleotide, and M' represents the nucleotide complementary to the substituted nucleotide, and (St) represents the genome side stem sequence. In addition, the area enclosed with square (☐) represents that it does not form base pair with the probe, but forms the stem structure or the loop structure.

As mentioned above, in the case where the mutant-type DNA is a DNA which has a substituted nucleotide, and the hybrid which has the stem structure in the probe side is formed, the hybrid further comprises the hybrid which forms further the stem structure or the loop structure in the genome side. The details will be described in (IV).

(II) In the Case where DNA is a Mutant-Type DNA which has the Deleted Nucleotide Region (II-1) In the Case where the Hybrid which has the Stem Structure in the Probe Side is Formed (a) In the Case where at Least the Mutant-Type Hybrid Forms the Stem Structure In the case where the mutant-type DNA is the one which has the deleted nucleotide region, and at the time when the probe has hybridized, the stem structure is formed in the probe side, and at least the mutant-type hybrid forms the stem structure; the probe pertaining to the present invention to be used has, for example, the following structure.

$$3'\ \text{1stSS}_{211}\text{-X'}_{211}\text{-DM'-X'}_{212}\text{-2ndSS}_{211}\ 5'$$

($\text{1stSS}_{211}$, $\text{2ndSS}_{211}$ represent the single-stranded nucleotide sequence which is complementary to the wild-type DNA and the mutant-type DNA, respectively; $\text{X'}_{211}$ and $\text{X'}_{212}$ represent arbitrary nucleotides, respectively; DM' represents the nucleotide sequence which is complementary to the deleted nucleotide region, and which forms the stem structure.)

The above-described deleted nucleotide region means the nucleotide region in the wild-type DNA which is deleted in the mutant-type DNA.

When said probe is hybridized with the mutant-type DNA, the following mutant-type hybrid is formed.
Mutant-Type Hybrid Probe:   $3'\ \text{1stSS}_{211}\text{-X'}_{211}\text{-DM'-X'}_{212}\text{-2ndSS}_{211}\ 5'$ Genome:  $5'\ \text{1stDS}_{211}\text{-X}_{211}\text{-X}_{212}\text{-2ndDS}_{211}\ 3'$ (In said hybrid, $\text{1stSS}_{211}$, $\text{2ndSS}_{211}$, $\text{X'}_{211}$, $\text{X'}_{212}$, and DM' are the same as described above. $\text{1stDS}_{211}$, $\text{2ndDS}_{211}$ represent the nucleotide sequence region which forms complementary double strand with $\text{1stSS}_{211}$, $\text{2ndSS}_{211}$, respectively; $\text{X}_{211}$ and $\text{X}_{212}$ represent respective nucleotides, and $\text{X'}_{211}$ and $\text{X}_{211}$, and $\text{X'}_{212}$ and $\text{X}_{212}$ are complementary nucleotides, respectively.)

In the above-described hybrid, the nucleotide sequence complementary to the deleted nucleotide region forms the stem structure.

When the above-described probe is hybridized with the wild-type DNA, the following wild-type hybrid is formed.
Wild-Type Hybrid Probe:   $3'\ \text{1st-SS}_{211}\text{-X'}_{211}\text{-DM'-X'}_{212}\text{-2ndSS}_{211}\ 5'$ Genome:  $5'\ \text{1stDS}_{211}\text{-X}_{211}\text{-DM-X}_{212}\text{-2ndDS}_{211}\ 3'$ (In said hybrid, $\text{1stSS}_{211}$, $\text{2ndSS}_{211}$, $\text{1stDS}_{211}$, $\text{2ndDS}_{211}$, $\text{X'}_{211}$ and $\text{X'}_{212}$ are the same as described above. $\text{X}_{211}$ and $\text{X}_{212}$ represent nucleotide, respectively, and these are complementary to $\text{X'}_{211}$ and $\text{X'}_{212}$, respectively. DM represents the deleted nucleotide region; and DM' is the nucleotide complementary to the deleted nucleotide region, which forms base pair with DM).

The above-described hybrid does not form the stem structure because the probe and genome can form base pairs completely.

(b) In the Case where at Least the Wild-Type Hybrid Forms the Stem Structure

In the case where the mutant-type DNA is a DNA which has the deleted nucleotide region, and at the time when the probe is hybridized, the stem structure is formed in the probe side, and at least the wild-type hybrid forms the stem structure (the wild-type hybrid forms a designed stem structure); the probe pertaining to the present invention to be used has, for example, the following structure.

$$3'\ \text{1stSS}_{221}\text{-X'}_{221}\text{-DM'-St}_{P221}\text{-X'}_{222}\text{-2ndSS}_{221}\ 5'$$

($\text{1stSS}_{221}$, $\text{2ndSS}_{221}$ represents the single-stranded nucleotide sequence which is complementary to the wild-type DNA and the mutant-type DNA, respectively; and $\text{X'}_{221}$ and $\text{X'}_{222}$ represent the nucleotides, respectively. DM' represents the nucleotide sequence which is complementary to the deleted nucleotide region and $\text{St}_{P221}$ represents the probe side stem sequence.)

When said probe is hybridized with the mutant-type DNA, the following mutant-type hybrid is formed.
Mutant-Type Hybrid Probe:
$3'\ \text{1stSS}_{221}\text{-X'}_{221}\text{-DM'-St}_{P221}\text{-X'}_{222}\text{-2ndSS}_{221}\ 5'$ Genome:
$5'\ \text{1stDS}_{221}\text{-X}_{221}\text{-X}_{222}\text{-2ndDS}_{221}\ 3'$ ($\text{1stSS}_{221}$, $\text{2ndSS}_{221}$, $\text{X'}_{221}$, $\text{X'}_{222}$, DM' and $\text{St}_{P221}$ are the same as described above. $\text{1stDS}_{221}$, $\text{2ndDS}_{221}$ represent the nucleotide sequence region which forms complementary double strand with $\text{1stSS}_{221}$, $\text{2ndSS}_{221}$, respectively; $\text{X}_{221}$ and $\text{X'}_{222}$ represent nucleotide, and $\text{X'}_{221}$ and $\text{X}_{221}$, and $\text{X'}_{222}$ and $\text{X}_{222}$ are complementary nucleotides, respectively.).

In the above-described hybrid, DM'-$\text{St}_{P221}$ and $\text{St}_{P221}$, namely, the nucleotide sequence which is complementary to the deleted nucleotide region and the probe side stem sequence, are coupled together and form the stem structure or the loop structure.

When the above-described probe is hybridized with the wild-type DNA, the following wild-type hybrid is formed.
Wild-Type Hybrid Probe:
$3'\ \text{1stSS}_{221}\text{-X'}_{221}\text{-DM'-St}_{P221}\text{-X'}_{222}\text{-2ndSS}_{221}\ 5'$ Genome:
$5'\ \text{1stDS}_{221}\text{-X}_{221}\text{-DM-X}_{222}\text{-2ndDS}_{221}\ 3'$ ($\text{1stSS}_{221}$, $\text{2ndSS}_{221}$, $\text{1stDS}_{221}$, $\text{2ndDS}_{221}$, $\text{X'}_{221}$, $\text{X'}_{222}$ DM', and $\text{St}_{P221}$ are the same as described above. $\text{X}_{221}$ and $\text{X}_{222}$ represent nucleotide, respectively; and are complementary to $X'_{221}$ and $X'_{222}$, respectively. DM represents the deleted nucleotide region.).

In the above-described hybrid, since the probe side stem sequence forms the stem structure, the above-described hybrid has the stem structure which is designed by the probe.

As mentioned above, in the case where the mutant-type DNA is a DNA which has the deleted nucleotide region, and the hybrid which has the stem structure in the probe side is formed; the hybrid further comprises the hybrid which forms the stem structure or the loop structure in the genome side. The details will be described in (IV).

(II-2) In the Case where the Hybrid which has the Stem Structure in the Genome Side is Formed In the case where the mutant-type DNA is the one which has the deleted nucleotide region, and at the time when the probe has hybridized, the stem structure is formed in the genome side, and at least the wild-type hybrid forms the stem structure; the probe pertaining to the present invention to be used has, for example, the following structure.

$$3'\ 1stSS_{231}\text{-}2ndSS_{231}\ 5'$$

($1stSS_{231}$ represents single-stranded nucleotide sequence which does not comprise the deleted nucleotide region and which is complementary to the 3'-side of the mutant DNA, and $2ndSS_{231}$ represents single-stranded nucleotide sequence which does not comprise the deleted nucleotide region and which is complementary to the 5'-side of the mutant DNA, respectively.).

The above-described deleted nucleotide region means the nucleotide region in the wild-type DNA which is defected in the mutant-type DNA.

When said probe is hybridized with the mutant-type DNA, the following mutant-type hybrid is formed.
Mutant-Type Hybrid

```
Probe:    3' 1stSS₂₃₁-2ndSS₂₃₁ 5'
Genome:   5' 1stDS₂₃₁-2ndDS₂₃₁ 3'
```

(In said hybrid, $1stSS_{231}$ and $2ndSS_{231}$ are the same as described above. $1stDS_{231}$, $2ndDS_{231}$ represent the nucleotide sequence region which forms complementary double strand with $1stSS_{231}$, $2ndSS_{231}$, respectively.)

The above-described hybrid does not form the stem structure because the probe and the genome can form the base pairs completely.

When the above-described probe is hybridized with the wild-type DNA, the following wild-type hybrid is formed.
Wild-Type Hybrid

```
Probe:    3' 1stSS₂₃₁-2ndSS₂₃₁ 5'
Genome:   5' 1stDS₂₃₁-DM-2ndDS₂₃₁ 3'
```

(In said hybrid, $1stSS_{231}$, $2ndSS_{231}$, 1stDS231, and 2ndDS231 are the same as described above. DM represents a sequence which is the deleted nucleotide region, and which forms the stem structure.)

In the above-described hybrid, since the deleted nucleotide region forms the stem structure in the genomic DNA side, said hybrid has the stem structure.

As mentioned above, in the case where the mutant-type DNA is a DNA which has the deleted nucleotide region, and which forms the hybrid having the stem structure in the genome side; the hybrid further includes the hybrid which forms the stem structure or the loop structure in the genome side. The details will be described in (IV).

(III) In the Case where DNA is a Mutant-Type DNA which has the Inserted Nucleotide Region (III-1) In the Case where the Hybrid which has the Stem Structure in the Genome Side is Formed (a) In the Case where at Least the Mutant-Type Hybrid Forms the Stem Structure In the case where the mutant-type DNA is a DNA which has the inserted nucleotide region, and at the time when the probe has hybridized, at least the mutant-type hybrid which has the stem structure in the genome side is formed, the probe pertaining to the present invention to be used has, for example, the following structure.

$$3'\ 1stSS_{311}\text{-}X'_{311}\text{-}X'_{312}\text{-}2ndSS_{311}\ 5'$$

($1stSS_{311}$, $2ndSS_{311}$ represent the single-stranded nucleotide sequence which is complementary to the wild-type DNA and the mutant-type DNA, respectively; $X'_{311}$ and $X'_{312}$ each represents nucleotide.)

When said probe is hybridized with the mutant-type DNA, the following mutant-type hybrid is formed.
Mutant-Type Hybrid

```
Probe:
3' 1stSS₃₁₁-X'₃₁₁      -X'₃₁₂-2ndSS₃₁₁ 5'

Genome:
5' 1stDS₃₁₁-X₃₁₁- IM -X₃₁₂-2ndDS₃₁₁ 3'
```

(In the hybrid, $1stSS_{311}$, $2ndSS_{311}$, $X'_{311}$ and $X'_{312}$ are the same as described above. $1stDS_{311}$, $2ndDS_{311}$ represent the nucleotide sequence region which forms complementary double strand with $1stSS_{311}$ and $2ndSS_{311}$, respectively; $X_{311}$ and $X_{312}$ represent nucleotide, respectively; and $X'_{311}$ and $X_{311}$, and $X'_{312}$ and $X_{312}$ are complementary nucleotides. 1M represents a sequence of the inserted nucleotide region.).

In said hybrid, the sequence of the inserted nucleotide region forms the stem structure.

When the above-described probe is hybridized with the wild-type DNA, the following wild-type hybrid is formed.
Wild-Type Hybrid

```
Probe:
3' 1stSS₃₁₁-X'₃₁₁ -X'₃₁₂-2ndSS₃₁₁ 5'

Genome:
5' 1stDS₃₁₁-X₃₁₁ -X₃₁₂-2ndDS₃₁₁ 3'
```

($1stSS_{311}$, $2ndSS_{311}$, $1stDS_{311}$, $2ndDS_{311}$, $X'_{311}$ and $X'_{312}$ are the same as described above. $X_{311}$ and $X_{312}$ represent nucleotide, respectively; and represents nucleotide which is complementary to $X'_{311}$ and $X'_{312}$, respectively.)

In said hybrid, since the probe and the genome form base pairs completely, the stem structure will not be formed.

(b) In the Case where at Least the Wild-Type Hybrid Forms the Stem Structure

In the case where the mutant-type DNA is the one which has the inserted nucleotide region, and at the time when the probe has hybridized, the stem structure is formed in the probe side, and at least the wild-type hybrid forms the stem structure (the wild-type hybrid forms a designed stem structure); the probe pertaining to the present invention to be used has, for example, the following structure.

$$3'\ 1stSS_{321} - X'_{322}\text{-}2ndSS_{321}\ 5'$$

($1stSS_{321}$, $2ndSS_{321}$ represent the single-stranded nucleotide sequence which is complementary to the wild-type DNA and the mutant-type DNA, respectively; and $X'_{321}$ and $X'_{322}$ represents nucleotide, respectively.)

When said probe is hybridized with the mutant-type DNA, the following mutant-type hybrid is formed.
Mutant-Type Hybrid

```
Probe:
3' 1stSS₃₂₁-X'₃₂₁        -X'₃₂₂-2ndSS₃₂₁ 5'

Genome:
5' 1stDS₃₂₁-X₃₂₁- St_G321-X₃₂₂-2ndDS₃₂₁ 3'
```

(In said hybrid, $1stSS_{321}$, $2ndSS_{321}$, $X'_{321}$, and $X'_{32}2$ are the same as described above. $1stDS_{321}$, $2ndDS_{321}$ represent the nucleotide sequence region which forms complementary double strand with $1stSS_{321}$ and $2ndSS_{321}$, respectively; $X_{321}$ and $X_{322}$ represent nucleotide, and these are the nucleotide complementary to $X'_{321}$ and $X'_{322}$, respectively. IM represents the sequence of the inserted nucleotide region, and $St_{G321}$ represents the genome side stem sequence.)

In said hybrid, IM-$St_{G321}$ nucleotide chain, namely, the inserted nucleotide region and the genome-type hybrid are coupled, and thereby the stem structure or the loop structure is formed.

When the above-described probe is hybridized with the wild-type DNA, the following wild-type hybrid is formed.
Wild-Type Hybrid

```
Probe:
3' 1stSS₃₁₁-X'₃₂₁      -X'₃₂₂-2ndSS₃₂₁ 5'

Genome:
5' 1stDS₃₂₁- St_G321-X₃₂₂-2ndDS₃₂₁ 3'
```

(In said hybrid, $1stSS_{321}$, $2ndSS_{321}$, $1stDS_{311}$, $2ndDS_{321}$, $X'_{321}$, $X'_{322}$, $X_{321}$, $X_{322}$ and $St_{G321}$ are the same as described above.)

In said hybrid, the genome side stem sequence forms the stem structure.

As mentioned above, in the case where the mutant-type DNA is a DNA which has the inserted nucleotide region, and which forms the hybrid having the stem structure in the genome side; the hybrid further includes the one which forms the stem structure or the loop structure in the probe side. The details will be described in (IV).

(III-2) In the Case where the Hybrid which has the Stem Structure in the Probe Side is Formed (a) In the Case where at Least the Wild-Type Hybrid Forms the Stem Structure In the case where the mutant-type DNA is the one which has the inserted nucleotide region, and at the time when the probe has hybridized, the stem structure is formed in the probe side, and at least the wild-type hybrid forms the stem structure, the probe pertaining to the present invention to be used has, for example, the following structure.

$$3'\ 1stSS_{321}\text{-}X'_{321}\text{-}IM'_{321}\text{-}X'_{322}\text{-}2ndSS_{321}\ 5'$$

($1stSS_{321}$, $2ndSS_{321}$ represent the single-stranded nucleotide sequence which is complementary to the wild-type DNA and the mutant-type DNA, respectively; $X'_{321}$ and $X'_{322}$ represents arbitrary nucleotide, respectively; $IM'_{321}$ represents the nucleotide sequence which is complementary to the inserted nucleotide region, and which forms the stem structure.)

When said probe is hybridized with the mutant-type DNA, the following mutant-type hybrid is formed.
Mutant-Type Hybrid

```
Probe:
3' 1stSS₃₂₁-X'₃₂₁-IM'₃₂₁-X'₃₂₂-2ndSS₃₂₁ 5'

Genome:
5' 1stSS₃₂₁-X₃₂₁-IM₃₂₁-X₃₂₂-2ndSS₃₂₁ 5'
```

(In the hybrid, $1stSS_{321}$, $2ndSS_{321}$, $X'_{321}$, $X'_{322}$, and $IM'_{321}$ are the same as described above. $1stDS_{321}$, $2ndDS_{321}$ represent the nucleotide sequence region which forms complementary double strand with $1stSS_{321}$ and $2ndSS_{321}$, respectively; $X_{321}$ and $X_{322}$ represent the nucleotides, respectively; and $X'_{321}$ and $X_{321}$, and $X'_{322}$ and $X_{322}$ are complementary nucleotides. $IM_{321}$ represents the sequence of the inserted nucleotide region.).

In said hybrid, since the probe and the genome form base pairs completely, the stem structure is not formed.

When the above-described probe is hybridized with the wild-type DNA, the following wild-type hybrid is formed.
Wild-Type Hybrid

```
Probe:
3' 1stSS₃₂₁-X'₃₂₁-IM'₃₂₁-X'₃₂₂-2ndSS₃₂₁ 5'

Genome:
5' 1stDS₃₂₁-X₃₂₁-            -X₃₂₂-2ndDS₃₂₁ 3'
```

(In the hybrid, $1stSS_{321}$, $2ndSS_{321}$, $X'_{321}$, $X'_{322}$, $IM'_{321}$, $1stDS_{321}$, $2ndDS_{321}$, $X_{321}$, and $X_{322}$ are the same as described above.).

In said hybrid, the nucleotide chain which is complementary to the inserted nucleotide region forms the stem structure.

(b) In the Case where at Least the Mutant-Type Hybrid Forms the Stem Structure

In the case where the mutant-type DNA is the one which has the inserted nucleotide region, and at the time when the probe has hybridized, the stem structure is formed in the probe side, and at least the mutant-type hybrid forms the stem structure (the mutant-type hybrid forms the stem structure), the probe pertaining to the present invention to be used has, for example, the following structure.

$$3'\ 1stSS_{331}\text{-}X'_{331}\text{-}IM'_{331}\text{-}Stp_{131}\text{-}X'_{332}\text{-}2ndSS_{331}\ 5'$$

($1stSS_{331}$, $2ndSS_{331}$ represent the single-stranded nucleotide sequence which is complementary to the wild-type DNA and the mutant-type DNA, respectively; and $X'_{331}$ and $X'_{332}$ represents arbitrary nucleotide, respectively; $IM'_{331}$ represents the nucleotide sequence which is complementary to the substituted nucleotide region; and $St_{P331}$ represents the probe side stem sequence.).

$$3'\ 1stSS_{321}\text{-}X'_{321}\text{-}IM'_{321}\text{-}X'_{322}\text{-}2ndSS_{321}\ 5'$$

($1stSS_{331}$, $2ndSS_{331}$, $X'_{331}$, $X'_{332}$, $IM'_{331}$, and $Stp_{331}$ are the same as described above.).

When the above-described probe is hybridized with the mutant-type DNA, the following mutant-type hybrid is formed.

Mutant-Type Hybrid

```
Probe:
3' 1stSS331-X'331-IM'331-Stp331-X'332-2ndSS331 5'

Genome:
5' 1stDS331-X331-IM331          -X332-2ndDS331 3'
or

Probe:
3' 1stSS331-X'331-Stp331-IM'331-X'332-2ndSS331 5'

Genome:
5' 1stDS331-X331         -IM331 -X332-2ndDS331 3'
```

(In the hybrid, $1stSS_{331}$, $2ndSS_{331}$, $X'_{331}$, $X'_{332}$, and $IM'_{331}$ are the same as described above. $1stDS_{331}$ and $2ndDS_{331}$ represent the nucleotide sequence region which forms complementary double strand with $1stSS_{331}$ and $2ndSS_{331}$, respectively; $X_{331}$ and $X_{332}$ represent the nucleotides, respectively, and $X'_{331}$ and $X_{331}$, and $X'_{332}$ and $X_{332}$ are complementary nucleotides, respectively. $IM_{331}$ is a sequence of the inserted nucleotide region which represents the nucleotide complementary to IM'331; and $Stp_{331}$ represents the probe side stem sequence.).

In said hybrid, since the probe side stem sequence forms the stem structure, said hybrid has the stem structure which is designed in the probe.

When the above-described probe is hybridized with the wild-type DNA, the following wild-type hybrid is formed.
Wild-Type Hybrid

```
Probe:
3' 1stSS331-X'331-IM'331-Stp331-X'332-2ndSS331 5'

Genome:
5' 1StDS331-X331-                 -X332-2ndDS331 3'
or

Probe:
3' 1stSS331-X'331-Stp331-IM'331-X'332-2ndSS331 5'

Genome:
5' 1StDS331-X331                  -X332-2ndDS331 3'
```

(In the hybrid, $1stSS_{331}$, $2ndSS_{331}$, $X'_{331}$, $X'_{332}$, $IM'_{331}$, $Stp_{331}$, $1stDS_{331}$, $2ndDS_{331}$, $X_{331}$ and $X_{332}$ are the same as described above.).

In the above-described mutant-type hybrid, the probe side stem sequence and the inserted nucleotide region are coupled, and thereby the stem structure or the loop structure is formed.

As mentioned above, in the case where the mutant-type DNA is a DNA which has the inserted nucleotide region, and which forms the hybrid having the stem structure in the probe side; the hybrid further includes the hybrid which forms the stem structure or the loop structure in the genome side. The details will be described in (IV).

(IV) In the Case where the Stem Structure or the Loop Structure is Further Formed in the Chain Opposite to the Nucleotide Chain which has the Stem Structure In the hybrid pertaining to the present invention described in above (I) to (III), the stem structure or the loop structure, preferably the stem structure, may be further formed in the chain in the opposite side of sequence which has the stem structure, namely, it may be formed in the probe side when the stem structure is present in the genome side, or it may be formed in the genome side when the stem structure is present in the probe side, and thereby sharpness (precision) of separation of the mutant-type hybrid from the wild-type hybrid can be increased.

In that case, as for the probe, when the stem structure is present in the genome side, a sequence for forming stem sequence or the loop may be further inserted in the sequence of the above-described probe, and when the stem structure is present in the probe side, to form the stem structure or the loop structure in the genome, a complementary chain corresponding to the sequence which forms these structure may be removed from the probe.

Specifically, in the case where, for example, the mutant-type DNA is the one which has the inserted nucleotide region, and at the time when the probe has hybridized, at least the mutant-type hybrid which has the stem structure in the genome side is formed (corresponding to the above-described III-1), to form further the stem structure or the loop structure in the probe side, the probe pertaining to the present invention to be used may be, for example, the one which has the following structure.

```
3' 1stSS411-X'411 - Stop - X'412 -2ndSS411 5'
```

($1stSS_{411}$, $2ndSS_{411}$ represent the single-stranded nucleotide sequence which is complementary to the wild-type DNA and the mutant-type DNA, respectively; $X'_{411}$ and $X'_{412}$ represent respective nucleotides; $St_{op}$ represents the probe side stem sequence, or a sequence which forms the loop structure in the probe side.).

When said probe is hybridized with the mutant-type DNA, the following mutant-type hybrid is formed.
Mutant-Type Hybrid

```
Probe:
3' 1stSS411-X'411 - Stop--X'412-2ndSS411 5'

Genome:
5' 1StDS411-X411- IM     -X412-2ndDS411 3'
```

(In the hybrid, $1stSS_{411}$, $2ndSS_{411}$, $X'_{411}$, and $X'_{412}$ are the same as described above. $1stDS_{311}$, $2ndDS_{311}$ represent the nucleotide sequence region which forms complementary double strand with $1stSS_{31}$ and $2ndSS_{311}$, respectively; $X_{411}$ and $X_{412}$ represent the nucleotides, respectively; and $X'_{411}$ and $X_{411}$, and $X'_{412}$ and $X_{412}$ are complementary nucleotides. IM represents the sequence of the inserted nucleotide region.).

In said hybrid, on the genome side, the sequence of the inserted nucleotide region forms the stem structure, and on the probe side, the sequence which forms the stem structure in the probe side or the sequence which forms the loop structure in the probe side forms the stem structure or the loop structure.

When the above-described probe is hybridized with the wild-type DNA, the following wild-type hybrid is formed.
Wild-Type Hybrid

```
Probe:
3' 1stSS411-X'411- Stop --X'412 -2ndSS411 5'

Genome:
5' 1stDS411-X411-          -X412 -2ndDS411 3'
```

($1stSS_{411}$, $2ndSS_{411}$, $1stDS_{411}$, $2ndDS_{411}$, $X'_{411}$, and $X'_{412}$ are the same as described above.).

In said hybrid, on the probe side, the probe side stem sequence or the sequence which forms the loop structure in the probe side forms the stem structure or the loop structure.

In addition, as for the case where the stem structure or the loop structure is intended to be formed in the genome side, for example, in the case where the mutant-type DNA is the one which has a substituted nucleotide, and at the time when the probe side has hybridized, the stem structure is formed in the probe side (corresponding to the above-described I-1), and further the stem structure or the loop structure is intended to be formed in the genome side, the nucleotide chain complementary to the sequence which forms the stem structure or the loop structure may be removed from the probe side, for example, the probe in which 4 to 60 mer, preferably 6 to 30 mer, more preferably 6 to 20 mer of nucleotide chain coupled to the probe side stem sequence is removed may be used.

[Method for Detecting Mutant DNA Pertaining to the Present Invention]

The method for detecting mutant DNA of the present invention is performed by the following steps:

(1) A sample containing the single-stranded DNA having substituted nucleotide, deleted nucleotide region, or inserted nucleotide region (mutant-type DNA) or/and a wild-type single-stranded DNA corresponding thereto (wild-type DNA) are contacted with the probe which is capable of hybridizing with both single-stranded DNA to form the hybrid with the mutant-type DNA (mutant-type hybrid) or/and the hybrid with the wild-type DNA (wild-type hybrid);

(2) Obtained mutant-type hybrid or/and wild-type hybrid are separated by electrophoresis method; and (3) The presence or absence of the mutant-type DNA in the sample is determined.

As the method in the above-described (1) for forming the mutant-type hybrid or/and the wild-type hybrid by contacting a sample containing the mutant-type single-stranded DNA or/and the wild-type DNA with the probe, the probe pertaining to the present invention is added to a solution containing the mutant-type DNA or/and the wild-type DNA so that it makes concentration in the solution to be 20 nM to 2 µM, preferably 100 nM to 500 nM; after that, by carrying out 1 to 4 cycle of reactions, for example at 90° C. to 100° C. for 2 minutes to 4 minutes (thermal denaturation), at 30 C to 55° C. for 1 second to 30 seconds (DNA molecule association reaction), and at 65° C. to 75° C. for 1 minute to 4 minutes (template elongation reaction by residual polymerase) (hereinafter, said reaction is sometimes referred to as stem-loop hybrid reaction or stem-loop hybrid method), the mutant-type hybrid or/and the wild-type hybrid may be formed. In addition, since the above-described DNA molecule association reaction in the stem-loop hybrid method progresses even under the condition at the time of template elongation reaction by residual polymerase, the stem-loop hybrid method may be performed by carrying out 1 to 4 cycle of reactions at 90° C. to 100° C. for 2 minutes to 4 minutes (thermal denaturation, DNA molecule association reaction) and at 65° C. to 75° C. for 1 minute to 4 minutes (template elongation reaction by residual polymerase). In addition, in the stem-loop hybrid reaction, the more the number of cycles, larger amount of the mutant-type hybrid or the wild-type hybrid which is the reaction product can be obtained. However, in four or more cycles, since the amount of the product almost remains, usually 2 to 4 cycle is preferable, and 3 to 4 cycle is more preferable.

More specifically, first, to 20 µL to 40 µl of buffer solution such as, for example, 10 mM to 50 mM Tris buffer solution (pH 8.4 to 9.0) in which, for example, 100 ng of mutant-type DNA or/and wild-type DNA is dissolved, the probe pertaining to the present invention is added so as to set the concentration in solution to 20 nM to 2 µM, preferably 100 nM to 500 nM, more preferably 100 nM to 200 nM. Then, for example, by carrying out 1 to 4 cycle of reactions at 90° C. to 100° C. for 2 minutes to 4 minutes (thermal denaturation), at 30° C. to 55° C. for 1 second to 30 seconds (DNA molecule association reaction), and at 65° C. to 75° C. for 1 minute to 4 minutes (template elongation reaction by residual polymerase), the mutant-type hybrid or/and the wild-type hybrid are formed.

For the mutant-type single-stranded DNA or the wild-type DNA in the above-described reaction (1), the one which is made amplified according to well-known PCR reaction as mentioned above may be used, and in such case, specifically the step of (1) is carried out as follows. That is, for example, 1 pg to 100 pg of DNA to be used as a template is dissolved in 20 µL to 40 µL of reaction solution; and this solution is further added with, usually 1 pmol to 100 pmol, preferably 1 pmol to 50 pmol of each 2 kinds of primers (Forward and Reverse), and usually 4 kinds of deoxyribonucleotide triphosphate (dNTPs) so that it provides each 0.01 nmol to 50 nmole, preferably 0.1 nmol to 20 nmol; in a buffer solution such as Tris HCl buffer solution containing 1 U to 5 U of thermostable DNA polymerase such as Taq DNA polymerase, KOD DNA polymerase, for example, a reaction cycle composing, (1) at 93° C. to 98° C. for 10 seconds to 10 minutes→(2) 50° C. to 60° C. for 10 seconds to 3 minutes→65° C. to 75° C. for 1 minute to 5 minutes is repeated for 30 to 40 times; and thus step (1) is performed. After that, to the obtained reaction solution, 0.1 to 5 times more amount of the probe pertaining to the present invention than the PCR primer, for example, usually 0.1 pmol to 500 pmol, preferably 0.1 pmol to 50 pmol is added, and the stem-loop hybrid reaction is carried out by the same way as described above.

In addition, when mutant-type single-stranded DNA or/and wild-type DNA is amplified by the PCR reaction as described above, the stem-loop hybrid reaction can also be performed simultaneously with said PCR reaction. In that case, as for the probe pertaining to the present invention, the one which is modified at 3'-terminus and 5'-terminus with phosphate group and the like is utilized, and under the presence of said probe, the above-described PCR reaction may be carried out. Specifically, for example, 1 pg to 100 pg of the DNA to be used as a template is dissolved in 20 µL to 40 µL of reaction solution; and this solution is further added with, usually 1 pmol to 100 pmol, preferably 1 pmol to 50 pmol of each 2 types of primers (Forward and Reverse), 4 kinds of deoxyribonucleotide triphosphate (dNTPs) so that it provides each usually 0.01 nmol to 50 nmole, preferably 0.1 nmol to 20 nmol, and usually 0.1 nmol to 500 pmol, preferably 0.1 pmol to 50 pmol of the probe pertaining to the present invention which is modified at 3'-terminus and 5'-terminus; and the mixture is reacted in a buffer solution such as 10 to 50 m of Tris HCl buffer solution (pH 8.4 to 9.0) containing, for example, 1 U to 5 U of thermostable DNA polymerase, for example, in a reaction cycle of (1) at 93° C. to 98° C. for 10 seconds to 10 minutes→(2) 50° C. to 60° C. for 10 seconds to 3 minutes→ (3) 65° C. to 75° C. for 1 minute to 5 minutes is repeated for 30 to 40 times.

The electrophoresis method in the above-described (2) includes, although there is no limitation specifically so long as it can separate the above-described mutant-type hybrid from the wild-type hybrid, for example, electrical separation methods such as electrophoresis method and dielectrophoresis method comprising isoelectric focusing, SDS-polyacrylamide electrophoresis, agarose gel electrophoresis, acrylamide electrophoresis, capillary electrophoresis, and capillary chip electrophoresis; however, from the points of cooling efficiency, applicable high voltage and separation efficiency, capillary electrophoresis, capillary-chip electrophoresis are preferable, and capillary chip electrophoresis which is suitable for micro-scale sample analysis is particularly preferable. It should be noted that, the conditions of these separation methods may be performed according to the method well-known per se, for example, the capillary-chip electrophoresis may be performed according to the method described in WO2007/027495, etc.

As for the detection method in the above-described (3), any kind of detection method can be used if it is a method well-known per se. The detection may be performed by an apparatus such as differential refractive index detector, fluorescence detector, UV detector, and among them, detection by UV detector, fluorescence detector are preferable, and detection by fluorescence detector is more preferable.

In performing fluorescent detection, various fluorescence detection methods may be utilized. Detection may be performed by the method such as, for example, (I) a method in which after performing the reaction of the above-described (1) using a previously fluorescence-labeled probe, fluorescence is detected by carrying out the electrophoresis of (2); (II) a method in which after performing the reaction of (1) using the probe, electrophoresis is carried out, and after electrophoresis, DNA is labeled by intercalator, etc.

The fluorescence label of the probe employed here includes, for example, cyanine dye. The cyanine dye mentioned here is a compound in which two heterocyclic rings are coupled through a methine group or a polymethine group, and at least one of the heterocyclic rings is nitrogen-containing heterocycle, and the one, in which both of the above-described heterocyclic rings are nitrogen-containing heterocycle, is preferable. As a substituent group derived from above-described cyanine dye, for example, a dye derived from Cy-series dye described in U.S. Pat. No. 4,981,977, U.S. Pat. No. 5,268,486, U.S. Pat. No. 5,486,616, etc., a dye derived from Dy-series dye described in U.S. Pat. No. 6,083,485, etc., a dye derived from HiLyte-series dye described in WO2006/047452, and a dye derived from Alexa-series dye are preferable. In addition, the one derived from commercially available dyes may be utilized, for example, in the case where a dye derived from Cy-series dye is utilized, the one derived from Cy3, Cy3.5, Cy5, Cy5.5, Cy7, and so on [all of them are trade name of Amersham Biosciences]; as for a dye derived from Dy-series dye, the one derived from DY-700, DY-701, DY-730, DY-731, DY-732, DY-734, DY-750, DY-751, DY-752, DY-776, DY-780, DY-781, DY-782, and so on; as for a dye derived from HiLyte-series dye, the one derived from HiLyte Fluor 555, HiLyte Fluor 647, HiLyte Fluor 680, HiLyte Fluor 750, and so on (all of them are trade name of AnaSpec Inc.); as for a dye derived from Alexa-series dye, Alexa Fluor Dye 532, Alexa Fluor Dye 546, Alexa Fluor Dye 555, Alexa Fluor Dye 568, Alexa Fluor Dye 594, Alexa Fluor Dye 633, Alexa Fluor Dye 647, Alexa Fluor Dye 660, Alexa Fluor Dye 680, Alexa Fluor Dye 700, Alexa Fluor Dye 750, and so on [all of them are trade name of Molecular Probes]; are included as a desirable dye. Among them, a dye derived from Cy-series dye is preferable, among them a dye derived from Cy5 is preferable.

In addition, the intercalator employed in the above-described detection method may be the one which emits strong fluorescence by binding with nucleic acid chain, and specifically, acridine dye such as, for example, acridine orange, ethidium compound such as, for example, ethidium bromide, ethidium homodimer 1 (EthD-1), ethidium homodimer 2 (EthD-2), ethidium bromide monoazide (EMA), and dihydroethidium, iodine compound such as, for example, propidium iodide, hexidium iodide, for example, 7-amino actinomycin D (7-AAD), dimeric cyanine series dye such as, for example, POPO-1, BOBO-1, YOYO-1, TOTO-1, JOJO-1, POPO-3, LOLO-1, BOBO-3, YOYO-3, TOTO-3 (all of them are trade name of Molecular Probes Inc.), SYTOX series dye such as, for example, SYBR Gold, SYBR Green I and SYBR Green II, SYTOX Green, SYTOX Blue, and SYTOX Orange (all of them are trade name of Molecular Probes Inc.), are included. In addition, the one which bind to a minor groove in double helix of DNA [for example, 4',6'-diamidine-2-phenylindole, (DAPI: trade name of Molecular Probes Inc.), pentahydrate(bis-benzimide) (Hoechst 33258: trade name of Molecular Probes Inc.), trihydrochloride (Hoechst 33342: trade name of Molecular Probes Inc.), bisbezimide dye (Hoechst 34580: trade name of Molecular Probes Inc.) and so on], the one which bind specifically to adenine-thymine (A-T) sequence [for example, acridine dye such as 9-amino-6-chloro-2-methoxyacridine (ACMA), his-(6-chloro-2-methoxy-9-acridinyl) spermine (acridine homodimer), for example, hyroxystirbamidine etc.], can also be used in the same way as intercalator.

Specifically, the method for detecting mutant DNA of the present invention is carried out, for example, as follows.

That is, in the case where the detection of mutant DNA is carried out, for example, for human genomic DNA derived from cancer patient, the human genomic DNA which is extracted and refined by using a commercially available kit and the like is used as a sample, and the PCR reaction is performed. The sample for PCR reaction may be prepared, for example, by dissolving each primer for detection of target DNA (Forward and Reverse) usually by 100 to 1000 nM, each 4 kinds of deoxyribonucleotide triphosphate (dNTPs) usually by 0.1 to 500 nM, and Taq DNA polymerase 1 to 5 units in 20 μL of buffer solution such as Tris HCl buffer, and by adding 1 ng to 100 ng of human genomic DNA thereto. As for the PCR reaction, for example, by performing 30 to 40 cycles of a reaction cycle composed of (1) 93 to 98° C. for 10 to 30 seconds, (2) 50 to 60° C. for 10 to 30 seconds, and (3) 68 to 72° C. for 1 to 3 minutes, the target single-stranded DNA can be amplified. After the PCR reaction, by adding 0.1 to 10 times more amount of probe than the primer used in PCR, the hybrid reaction is performed. That is, for example, to the PCR product, the probe pertaining to the present invention is added so as to give a final concentration of 100 to 500 nM, and the mixture is reacted at 90 to 100° C. for 2 to 4 minutes, 30 to 55° C. for 1 to 30 seconds, 65 to 75° C. for 1 to 4 minutes, and by repeating the reaction for 1 to 4 cycles, the hybrid of DNA of detection target can be obtained. Obtained solution is separated by an appropriate separation method, for example by capillary chip electrophoresis, and by detecting using a fluorescence detector etc., the mutant-type DNA can be detected.

Hereinafter, the present invention will be explained in more detail by referring to Examples, Comparative Examples and so on, however, the present invention is not limited thereto in any way.

EXAMPLES

Example 1: Detection of Single Nucleotide Substitution Mutant DNA of KRAS Gene by the Probe which can Form the Hybrid Having the Stem Structure (1) Preparation of Human Genomic DNA Derived from a Colorectal Cancer Patient The human genomic DNA derived from a colorectal cancer patient was prepared using QIAGEN QIAamp DNA Mini Kit. A 25 mg of frozen cancer tissue was homogenized, then buffer solution attached to the kit was added and further proteinase K was added, and lysed completely at 56° C., and after treatment with RNaseA, deproteinization was carried out by buffer solution attached to the kit, then the centrifuged supernatant was extracted and refined by a spin column attached to the kit, and 50 ng/μL of the human genomic DNA was prepared as a template material. After the obtained purified genomic DNA was amplified by the PCR reaction described in next section (3), the amplified DNA was purified by the montage PCR of Millipore Corp. and used as a sample DNA, and using the primer KRAS-Rv [SEQ ID NO: 15] as a sequence primer, sequence check was performed by the same method as described later in Synthetic Example 1 (2), and it was confirmed that single nucleotide substitution (GTT) was present on the codon 12 of KRAS gene.

(2) Preparation of the Probe for Stem-Type Loop-Hybrid Reaction (SLH Reaction)

The probe mentioned below which was designed so that the probe binds with mutant nucleotide and that the loop which is formed at the time of hybridization will be the stem structure was used as the probe for the SLH reaction (IN-1):

[SEQ ID NO: 17]
aaggcctgctgaaaatgactgaatatataaacttgtggtagttggagctggtatatatataggcgtaggcaagagtgccctt gacgatacag Oligonucleotide synthesis of the above-described primers and probe was performed through the use of custom synthesis service of Sigma-Genosys Inc.

It should be noted that, when said probe is used, it is conceived that the stem structure shown in FIG. 16 is formed on the probe.

(3) SLH Reaction of Human Genomic DNA Derived from Colorectal Cancer Patient

Using the human genomic DNA derived from colorectal cancer patient prepared in the above-described (1) as a sample, the PCR reaction was carried out with the use of AccuPrime Taq Polymerase System (a kit for PCR reaction, produced by Invitrogen Corp.). That is, firstly, according to the product protocol of attachment to the kit, and using each 2 μL of 10 μM primers (KRAS-Fw: aaggcctgctgaaaatgactg [SEQ ID NO: 16] and KRAS-Rv: ggtcctgcaccagtaatatgca [SEQ ID NO: 15]) and 2 μL of PCR reaction buffer of attachment to the kit, 20 μL of reaction liquid for PCR was prepared. Then, 25 ng of the human genomic DNA derived from colorectal cancer patient was added and suspended in 20 μL of the reaction liquid for PCR, and used it as a sample for PCR. Oligonucleotide synthesis of the above-described primer and probe was performed through the use of custom synthesis service of Sigma-Genosys Inc. Using this sample for PCR, and with the use of DNA Thermal Cycler of MJ Research Inc. (DNA Engine PTC200), 36 cycles of PCR reaction was carried out under the following reaction condition.

| Reaction condition of the PCR: | |
| --- | --- |
| Thermals denaturation: | 95° C., 15 sec. |
| Annealing: | 55° C., 15 sec. |
| Polymerization reaction: | 68° C., 47 sec. |

After termination of the reaction, the SLH probe (ID.=IN-1: aaggcctgctgaaaatgactgaatatataaacttgtggtagttggagctgg-tatatatataggcgtaggcaagagtgccctt gacgatacag [SEQ ID NO: 17]) was added to the PCR product so that it gives a final concentration 200 nM, and then with the use of DNA Thermal Cycler (DNA Engine PTC200, produced by MJ Research, Inc.), 1 cycle of reaction was carried out on the following reaction condition.

| (SLH-reaction) | |
| --- | --- |
| PCR product | 4.5 μL |
| SLH probe | 0.5 μL of 2 μM stock |
| 105° C. | hot lid |
| 95° C. | 2 min. |
| 55° C. | 0 to 30 sec. |
| 68° C. | 4 min. |
| 4° C. | pause |

(4) Separation and Detection of the Hybrid Generated by the SLH Reaction (Microchip Electrophoresis)

The reaction product obtained in the above-described (3) was subjected to the microchip electrophoresis method with the use of Agilent 2100 Bioanalyzer systems (Agilent Technologies Inc.). In this electrophoresis method, Agilent DNA1000 Assay kit (produced by Agilent Technologies Inc.) which is the dedicated Reagent set was used, and according to the product protocol attached to the kit, 1.0 μL of each reaction products was applied. In addition, for peak analysis after electrophoresis, system attached Agilent 2100 Expert software was utilized, and waveform analysis and calculation of peak mobility were performed.

The results were shown in FIG. 1.

Comparative Example 1: Detection of Single Nucleotide Substitution Mutant DNA of KRAS Gene by the Probe (LH Probe) which can Form the Hybrid not Having the Stem Structure The probe described below which forms the loop structure at the time of the hybrid formation was used as the probe for LH reaction (Del-7).

LH probe ID. = Del-7:
[SEQ ID NO: 18]
aaggcctgctgaaaatgactgaatatataaacttgtggtagttggagctgg tggcgtaggcaagagtgccttgacgatacagct It should be noted that, when said probe is used, it is conceived that the loop structure of the structure shown in FIG. 17 is formed on the genomic DNA.

The human genomic DNA derived from colorectal cancer patient was measured by the same method as Example 1 except for using the above-described probe. The results were shown in FIG. 2.

Figure 2:
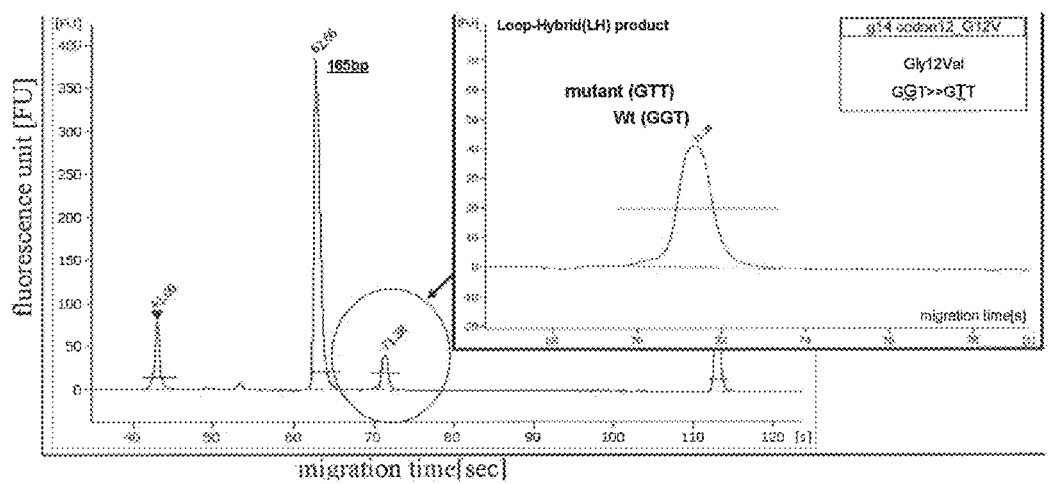
FIG. 2 is the result, obtained in Comparative Example 1, of electrophoresis carried out by microchip electrophoresis method for the hybrids of the wild-type DNA and the mutant-type DNA of KRAS gene which were prepared by the LH method using the probe which forms the hybrid not having the stem structure.

As is clear from the results shown in FIG. 1 and FIG. 2, it turned out that the human genomic DNA derived from colorectal cancer patient which could not be separated when the probe which does not form the hybrid having the stem structure (probe which forms only the loop structure, Del-7 [SEQ ID NO: 18]) was used (FIG. 2), could be separated when the probe which forms the hybrid having the stem structure (IN-1) [SEQ ID NO: 17] was used (FIG. 1). That is, it turned out that, by giving the stem structure to the hybrid, the capability of discrimination between the mutant-type DNA and the wild-type DNA was markedly improved as compared with the hybrid having mere loop structure.

Synthetic Example 1: Preparation of Sample Clone Having a Sequence of Mutant-Type DNA and Wild-Type DNA in the KRAS Gene As for the number of single nucleotide substitution in codon 12 and codon 13 of the KRAS gene exon 1, there exist 12 kinds of mutations in sum total of 3 kinds of mutations in each primary nucleotide and secondary nucleotide in the codon. And so, by the overlap extension PCR mutagenesis method (BioTechniques, Vol. 48, No. 6, June 2010, pp. 463-465) using synthetic oligonucleotides, the wild-type DNA sequence which was introduced with these mutant-type DNA was amplified by the PCR, and further, the amplification product was cloned into plasmid using pGEM-T Vector system (Promega Corp.), and sample clones having a sequence of 12 kinds of mutant-type DNA and wild-type DNA were obtained. The details of the procedure of this cloning were presented below.

That is, firstly, according to the protocol attached to QIAGEN QIAamp® DNA Blood Midi Kit, normal human genomic DNA was extracted and refined as described below from 2 mL of whole blood of normal healthy subject. Namely, to 2 mL of the blood, 200 μL of QIAGEN Protease provided in the kit was added and mixed. Subsequently, after adding 2.4 mL of Buffer AL of kit attachment and mixing completely, the mixture was incubated at 70° C. for 10 minutes. Then, after adding 2 mL of ethanol (96 to 100%) to the sample and mixed completely, the obtained solution was transferred to QIAamp Midi column in the centrifugal tube provided in the kit. Subsequently, the solution was centrifuged by 1,850×g (3,000 rpm) for 3 minutes, the QIAamp Midi column was removed, filtrate was discarded, the removed QIAamp Midi column was returned to the centrifuge tube, and then centrifuged by 1,850×g (3,000 rpm) for 3 minutes. Again, the QIAamp Midi column was removed, filtrate was discarded, and the removed QIAamp Midi column was returned to the 15 ml microcentrifuge tube. Subsequently, 2 mL of Buffer AW1 provided in the kit was added to the QIAamp Midi column, and centrifugal separation was carried out by 4,500×g (5,000 rpm) for 1 minute. Further, 2 mL of Buffer AW2 provided in the kit was added to the QIAamp Midi column, and centrifugal separation was carried out by 4,500×g (5,000 rpm) for 15 minutes. The QIAamp Midi column was transferred to a new microcentrifuge tube provided in the kit, and the tube containing filtrate was removed. At the end, at room temperature (15 to 25° C.), 300 μL of Buffer AE provided in the kit was placed directly on a membrane of QIAamp Midi column by pipetting. The lid was closed, and after incubation at room temperature for 5 minutes, centrifugal separation was carried out by 4,500×g (5,000 rpm) for 2 minutes, and thus, an eluate containing normal human genomic DNA was recovered from the whole blood of normal subject.

Subsequently, using the obtained normal human genomic DNA as a template, PCR reactions were carried out using the Platinum Taq polymerase system (Invitrogen Corp., Carlsbad, Calif.). According to the product protocol supplied with the kit, twelve PCR reactions were prepared by combining 1 μL of 10 μM primer 1204 [SEQ ID NO: 1] with 1 μL each of the following twelve 10 primers: primer 1211, 1212, 1213, 1221, 1222, 1223, 1311, 1312, 1313, 1321, 1322, and 1323 (see Table 1 below), with 5 μL of PCR reaction buffer supplied with the kit, 1 μL of 10 mM dNTPs, and 50 ng of normal human genomic DNA in 50 μL of the PCR reaction liquid.

TABLE 1

| Primer ID | Sequence | SEQ ID NO: |
|---|---|---|
| 1211 | acttgtggtagttggagctc | [SEQ ID NO: 2] |
| 1212 | acttgtggtagttggagctt | [SEQ ID NO: 3] |
| 1213 | acttgtggtagttggagcta | [SEQ ID NO: 4] |
| 1221 | cttgtggtagttggagctgc | [SEQ ID NO: 5] |
| 1222 | cttgtggtagttggagctgt | [SEQ ID NO: 6] |
| 1223 | cttgtggtagttggagctga | [SEQ ID NO: 7] |
| 1311 | tgtggtagttggagctggtc | [SEQ ID NO: 8] |
| 1312 | tgtggtagttggagctggtt | [SEQ ID NO: 9] |
| 1313 | tgtggtagttggagctggta | [SEQ ID NO: 10] |
| 1321 | ggagctggtgccgtaggcaag | [SEQ ID NO: 11] |
| 1322 | gtggtagttggagctggtgt | [SEQ ID NO: 12] |
| 1323 | gtggtagttggagctggtga | [SEQ ID NO: 13] |

Using this sample for PCR, the 35 cycles of PCR reaction was carried out for 12 kinds with the use of DNA Thermal Cycler of MJ Research Inc. (DNA Engine PTC200) on the following reaction condition.

| PCR reaction condition: | |
|---|---|
| Thermal denaturation: | 94° C., 20 sec. |
| Annealing: | 55° C., 20 sec. |
| Polymerization reaction: | 72° C., 20 sec. |

After dilution of these 12 kinds of PCR products by 1000 times, to increase the precision of mutation introducing efficiency, the PCR reaction was further performed using Pwo SuperYield DNA Polymerase (Roche) which is a polymerase with the highest replication accuracy. That is, as for the PCR reaction solution, using 1 μL of each 12 kinds of 10 μM primer pairs for mutation introduction, 5 μL of reaction buffer provided in the kit, and 1 μL of 10 mM dNTPs, and by adding 0.25 μL of 1000 times diluted corresponding mutation introduction PCR product described in the previous section, 50 μL of reaction liquid for PCR was prepared. Using this sample for PCR, the PCR reaction of 20 cycles was performed for the 12 kinds of mutation introduction PCR products on the following reaction condition.

| PCR reaction condition: | |
|---|---|
| Thermal denaturation: | 94° C., 15 sec |
| Annealing: | 55° C., 30 sec. |
| Polymerization reaction: | 68° C., 20 sec. |

Thereby, 12 kinds of high-definition mutation introduction PCR products in which the mutation have been introduced into the codon 12 or the codon 13 were obtained. Next, in order to amplify DNA which comprises an upstream part of the target final PCR product and has an overlapping part with the above-described mutation introduction PCR product by high-precision PCR, using the normal human genomic DNA as a template, and using Pwo SuperYield DNA Polymerase (Roche), and using each 1 μL of 10 μM primer 1203 N: gtactggtggagtatttgatagtg [SEQ ID NO: 14] and primer R: ggtcctgcaccagtaatatgca [SEQ ID NO: 15], and using 5 μL of PCR reaction buffer of attachment to the kit and 1 μL of 10 mM dNTPs; and 25 μL of normal human genomic DNA was added and suspended in 50 μL of reaction liquid for PCR and used as a sample for PCR; and the PCR reaction of 30 cycles was performed on the following reaction condition.

| PCR reaction condition: | |
| --- | --- |
| Thermal denaturation: | 94° C., 15 sec. |
| Annealing: | 55° C., 30 sec. |
| Polymerization reaction: | 68° C., 20 sec. |

Using 246 bp PCR product for the upstream side (1203N, R) obtained in this way, and each of 12 kinds of mutation introduction PCR products (162 to 175 bp) obtained in the preceding paragraph, and using Platinum Taq DNA Polymerase High Fidelity (Invitrogen Corp.), overlap extension PCR was performed. Reaction solution was made up using 5 μL of attached PCR reaction buffer, and 1 μL of 10 mM dNTPs, and 2 μL of 50 mM MgSO$_4$, and each 1 μL of PCR product for upstream side (1203N, R) and mutation introduction PCR products were added and suspended in 50 μL of reaction liquid for PCR and used as a sample for PCR; and the PCR reaction of 2 cycles was performed on the following reaction condition.

| PCR reaction condition: | |
| --- | --- |
| Thermal denaturation: | 94° C., 20 sec. |
| Annealing: | 50° C., 30 sec. |
| Polymerization reaction: | 68° C., 20 sec. |

After termination of this overlap extension PCR reaction, each 1 μL of 10 μM primer 1203 N: gtactggtggagtatttgatagtg [SEQ ID NO: 14] and 1204: catgaaaatggtcagagaaacc [SEQ ID NO: 1] was added to the above-described PCR reaction solution, and the PCR reaction of 25 cycles was performed continuously on the following reaction condition.

| PCR reaction condition: | |
| --- | --- |
| Thermal denaturation: | 94° C., 20 sec. |
| Annealing: | 55° C., 20 sec. |
| Polymerization reaction: | 68° C., 20 sec. |

The PCR product corresponding to the wild type was prepared with the use of Platinum Taq DNA Polymerase High Fidelity (Invitrogen, Corp.) by performing the PCR reaction of 30 cycles on the following reaction condition using 1 μL of each 10 μM primers 1203N and 1204, 5 μL of kit attached PCR reaction buffer, 1 μL of 10 mM dNTPs, and 2 μL of 50 mM MgSO$_4$, and as a template, 50 ng of normal human genomic DNA was added and suspended in 50 μL of reaction liquid for PCR.

| PCR reaction condition: | |
| --- | --- |
| Thermal denaturation: | 94° C., 20 sec. |
| Annealing: | 55° C., 20 sec. |
| Polymerization reaction: | 68° C., 20 sec. |

12 kinds of mutation introduction PCR products of 287 bp and 1 kind of wild type PCR product which were obtained by a series of these PCR reactions were inserted in plasmid vector pGEM-T easy by TA cloning method using pGEM-T Vector System (Promega, Corp.). Ligation reaction was carried out at room temperature for 1 hour using Rapid Ligation Buffer and T4 ligase which were provided in the kit.

Then, using E. coli JM109 Competent Cells which was produced by Toyobo Co., Ltd., and according to its product protocol, the transformation of E. coli JM109 Competent Cells was performed at 42° C. for 45 sec. using the above obtained recombinant DNA. After that, the obtained transformant was cultured on a plate of LB-agar medium containing 100 μg/mL ampicillin, 0.2 mM isopropyl-β-thiogalactopyranoside (IPTG), and 40 μg/mL X-Gal at 37° C. for 16 hours. After cultivation, by picking up white colonies, the transformant for the respective clones which were transduced with recombinant DNA inserted with the target DNA fragment were obtained. After that, using plasmid extraction kit (QIAprep Spin Miniprep) of Qiagen Corp., extraction and purification process of DNA was carried out.

Namely, the transformant for each clone which was proliferated overnight in 5 mL of LB liquid medium containing 100 μg/mL ampicillin was collected by centrifugation; and after bacteriolysis by alkaline method, the lysate was neutralized with acidic potassium acetate solution, and from their supernatant solution after centrifugation, the plasmid DNA was purified with a purification column provided in the kit.

(2) Confirmation of Sequence of 12 Kinds of Mutant DNA and Wild Type DNA

Next, using the sample clones with sequences of 12 kinds of mutant DNA and wild type DNA which were cloned in the above-described (1), sequence analysis by the Big Dye Terminator kit (produced by Applied Biosystems, Inc.) was performed in following procedure according to the product protocol.

| | |
| --- | --- |
| Sample DNA (respective clones): | 2 μL (100 ng) |
| T7 promoter primer: | 1 μL (5 pmol) |
| Premix: | 8 μL |

That is, deionized sterile water was added to the above-described mixture so that it might make total volume 20 μL, and using DNA thermal cycler (DNA Engine PTC200, produced by MJ Research, Inc.), the sequence reaction of 30 cycle was performed on the following reaction condition.

96° C., 2 min→(96° C., 10 sec→50° C., 5 sec→60° C., min)×25→4° C.

After refining the obtained sequence reaction product with the use of gel filtration column (produced by Qiagen, Corp.), using a sequencer (BaseStation, produced by MJ Research, Inc.) and according to the procedure manual, sequence decipherment of all candidate sequences was completed. As the result, it was confirmed that sample clones were produced possessing the twelve mutant-type DNA sequences and the two wild-type DNA sequences involving codons 12 and 13, shown in Tables 2 and 3, respectively.

TABLE 1

| Codon 12 mutant-type DNA. | Nucleotide substitution, Amino acid substitution |
|---|---|
| Mutant-type 1: KR12_AG | AGT, G12S |
| Mutant-type 2: KR12_CG | CGT, G12R |
| Mutant-type 3: KR12_TG | TGT, G12C |
| Mutant-type 4: KR12_GA | GAT, G12D |
| Mutant-type 5: KR12_GC | GCT, G12A |
| Mutant-type 6: KR12_GT | GTT, G12V |
| Wild-type (Wt): Wt | GGT |

TABLE 2

| Codon 13 mutant-type DNA | Nucleotide substitution, Amino acid substitution |
|---|---|
| Mutant-type 7: KR13_AG | AGC, G13S |
| Mutant-type 8: KR13_CG | CGC, G13R |
| Mutant-type 9: KR13_TG | TGC, G13C |
| Mutant-type 10: KR13_GA | GAC, G13D |
| Mutant-type 11: KR13_GC | GCC, G13A |
| Mutant-type 12: KR13_GT | GTC, G13V |
| Wild-type (Wt): Wt | GGC |

Example 2: Detection of Single Nucleotide Substitution Mutant DNA of KRAS Gene by Acryl Amide Gel Electrophoresis Method (1) SLH Reaction Using each sample clone prepared in the above-described Synthetic Example 1 as a sample, the PCR reaction was performed using the AccuPrime Taq DNA Polymerase System (a kit for the PCR reaction, produced by Invitrogen Corp.). That is, firstly, according to the product protocol of attachment to the kit, 1.0 μL of each 10 μM primer (KRAS-Fw;

aaggcctgctgaaaatgactg [SEQ ID NO: 16]

and KRAS-Rv; ggtcctgcaccagtaatatgca [SEQ ID NO: 15]) and the PCR reaction buffers 2.0 μL of attachment to a kit were used to prepare 20.0 μL of reaction liquid for PCR. Then each 2 pg of sample clone was added and suspended in 20 μL of reaction liquid for PCR, and used as a sample for PCR. In addition, for the oligo synthesis of the above-described primer and probe, custom synthesis service of Sigma-Genosys, Inc. was utilized. Using this sample for PCR, the PCR reaction of 30 cycles was performed with the use of DNA thermal cycler (DNA Engine PTC200, produced by MJ Research Inc.) on the following reaction condition.

| Reaction condition of the PCR: | |
|---|---|
| Thermal denaturation: | 95° C., 15 sec. |
| Annealing: | 55° C., 15 sec. |
| Polymerization reaction: | 68° C., 47 sec. |

After termination of the reaction, the SLH probe (ID.=IN-1:aaggcctgctgaaaatgactgaatataaacttgtggtagag gagctggtatatatataggcgtaggcaagagtgccttgacgatacag [SEQ ID NO: 17])

was added to the PCR product so that it gives a final concentration 200 nM, and then with the use of DNA Thermal Cycler (DNA Engine PTC200, produced by MJ Research Inc.), 1 cycle of reaction was carried out on the following reaction condition.

| (SLH-reaction) | |
|---|---|
| PCR product | 4.5 μL |
| SLH probe | 0.5 μL of 2 μM stock |
| 105° C. | hot lid |
| 95° C. | 2 min. |
| 55° C. | 30 sec. |
| 68° C. | 4 min. |
| 4° C. | pause |

(2) Separation and Detection of the Hybrid Generated by the SLH Reaction (Polyacrylamide Gel Electrophoresis)

Among various SLH reaction products obtained in the above-described (1), the products obtained by using 7 kinds of mutant-type DNA (KR12_CG, KR12_TG, KR12_GA, KR12_GC, KR12_GT, KR13_CG, and KR13_TG) and wild-type DNA of each 1.5 μL was added with 1.5 μL of gel loading buffer, and electrophoresis was performed in a non-denaturing 10% polyacrylamide gel. In addition, as a molecular mass marker, 1.5 μL of 100 bp ladder for size marker (produced by Promega Corp.) was loaded on the same gel, and electrophoresed. The polyacrylamide gel used was a compact gel (Compact gel C10L, produced by ATTO Corp.) of 6 cm×6 cm, and electrophoresis was carried out by a small electrophoretic equipment (Compact PAGE AE-7300, produced by ATTO Corp.) using Tris-glycine buffer solution (37.5 mM Tris and 288 mM glycine) as a buffer solution for electrophoresis at room temperature. After the electrophoresis, the gel was stained 10 minutes with SYBR Green I (TAKARA BIO Inc., F0513), and washed with water, then using a laser imaging scanner (Amersham Biosciences Corp., STORM 860), detection was performed by excitation wavelength of 450 nm and detection filter 520LP.

In addition, expected stem structure in each hybrid is as follows. In the table, a lower case letter represents the nucleotide which is not complementary to the genomic DNA, and the underlined part represents the sequence which is assumed to form the stem structure.

TABLE 4

| Type of probe | | Hybrid | Probe SEQ ID NO: |
|---|---|---|---|
| Wild type | Probe | GG<u>Tatatatata</u>GGC | SEQ ID NO: 31 |
| | Genomic DNA | CCA         CCG | |
| KR12_CG | Probe | c<u>GTatatatata</u>GGC | SEQ ID NO: 32 |
| | Genomic DNA | CCA         CCG | |
| KR12_TG | Probe | t<u>GTatatatata</u>GGC | SEQ ID NO: 33 |
| | Genomic DNA | CCA         CCG | |
| KR12_GA | Probe | Ga<u>Tatatatata</u>GGC | SEQ ID NO: 34 |
| | Genomic DNA | CCA         CCG | |
| KR12_GC | Probe | Gc<u>Tatatatata</u>GGC | SEQ ID NO: 35 |
| | Genomic DNA | CCA         CCG | |
| KR12_GT | Probe | Gt<u>Tatatatata</u>GGC | SEQ ID NO: 36 |
| | Genomic DNA | CCA         CCG | |
| KR13_CG | Probe | GG<u>Tatatatatac</u>GC | SEQ ID NO: 37 |
| | Genomic DNA | CCA         CCG | |

TABLE 4-continued

| Type of probe | Hybrid | Probe SEQ ID NO: |
|---|---|---|
| KR13_TG | Probe     GGTatatatatatGCS<br>Genomic DNA CCA            CCG | SEQ ID NO: 38 |

(3) Result

Figure 3:
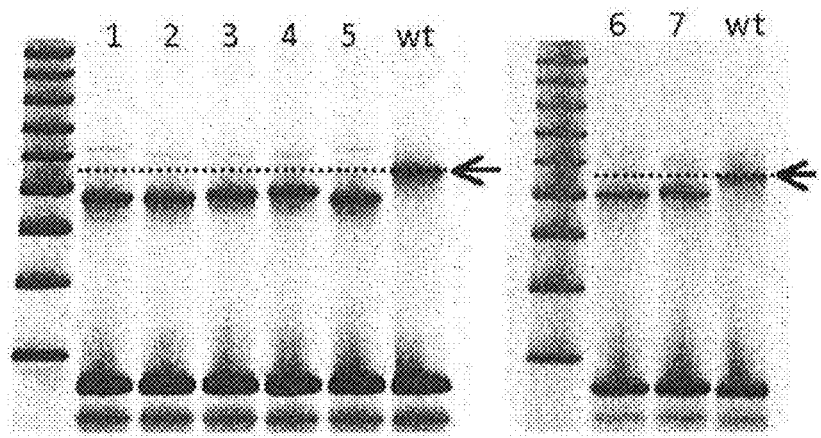
FIG. 3 is the result, obtained in Example 2, of electrophoresis carried out by polyacrylamide gel electrophoresis method for the hybrids of 7 kinds of mutant-type DNA and wild-type DNA of KRAS gene which were prepared by the LH method using the probe which forms the hybrid having the stem structure.

With respect to the sample clones which possess the sequence of 7 kinds of mutant DNA and wild type, the experimental results obtained by the electrophoresis after the SLH reaction were shown in FIG. 3. In addition, lane 1 to 5 in FIG. 3 shows the results of the use of KR12_CG, KR12_TG, KR12_GA, KR12_GC, KR12_GT, respectively, and lane 6 to 7 shows the results of the use of KR13_CG and KR13_TG, and wt shows the results of the use of wild type.

From the result shown in FIG. 3, it turned out that, when separation and detection of SLH reaction product obtained by the present invention is measured with the use of polyacrylamide gels electrophoresis, 5 kinds of mutant DNA in which the codon 12 are CGT, TGT, GAT, GCT, and GTT, respectively, and 2 kinds of mutant DNA in which the codon13 are CGC and TGC, respectively can be discriminated.

Example 3: Detection of Single Nucleotide Substitution Mutant DNA of KRAS Gene by Acryl Amide Gel Electrophoresis Method (1) SLH Reaction The SLH reaction of each sample clone prepared in Synthetic Example 1 was carried out by the same method as Example 2 except for using SLH probe

[ID.=IN-4:aaggcctgctgaaaatgactgaatataaacttgtggtagtt ggagctggttctgcagaaggtgtaggcaagagtgccttgacgatacag
(SEQ ID NO: 22)]

instead of using SLH probe (ID.=IN-1) in the above-described Example 2 (1).

It should be noted that, when the above-described probe SEQ ID NO: 22 is used, it is conceived that the stem structure shown in FIG. 18 is formed in the probe side.

(2) Separation and Detection of the Hybrid Generated by the SLH Reaction (Polyacrylamide Gel Electrophoresis)

The gel electrophoresis of the SLH reaction product was carried out by the same method as the above-described Example 2 (2) except for using 12 kinds of mutant-type DNA and wild-type DNA as the various kinds of SLH reaction products obtained in the above-described (1).

(3) Result

Figure 4:
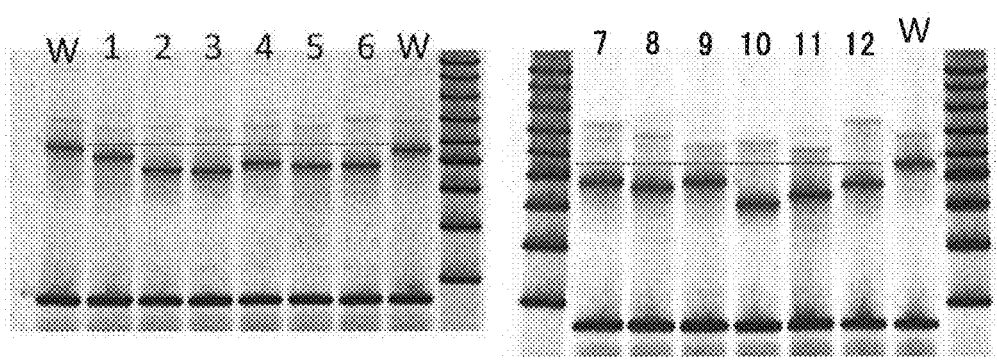
FIG. 4 is the result, obtained in Example 3, of electrophoresis, carried out by polyacrylamide gel electrophoresis method for the hybrids of 12 kinds of mutant-type DNA and wild-type DNA of KRAS gene which were prepared by the LH method using the probe (IN-4) which forms the hybrid having the stem structure.

With respect to the sample clones which possess the sequence of 12 kinds of mutant DNA and wild type, the experimental results obtained by the electrophoresis after the SLH reaction were shown in FIG. 4. In addition, lane 1 to 6 in FIG. 4 shows the results of the use of KR12_AG, KR12_CG, KR12_TG, KR12_GA, KR12_GC, KR12_GT, respectively, and lane 6 to 12 shows the results of the use of KR13_AG, KR13_CG, KR13_TG, KR13_GA, KR13_GC, KR13_GT, and wt shows the results of the use of the wild type.

From the result shown in FIG. 4, it turned out that, when separation and detection of SLH reaction product obtained by the present invention using the probe of the above-described IN-4 is performed by polyacrylamide gel electrophoresis, 6 kinds of mutant DNA in which the codon 12 are AGT, CGT, TGT, GAT, GCT, and GTT, respectively, and 6 kinds of mutant DNA in which the codon 13 are AGC, CGC, TGC, GAC, GCC, and GTC, respectively can also be discriminated.

Example 4: Detection of Various Kinds of Single Nucleotide Substitution Mutant DNA in the KRAS Gene (Microchip Electrophoresis Method)

The SLH reaction product obtained in the above-described Example 2 (1) was subjected to microchip electrophoresis method using Agilent2100 Bioanalyzer System (Agilent Technologies Inc.). In the present electrophoresis method, Agilent DNA1000 Assay kit (produced by Agilent Technologies Inc.) which is a reagent kit for exclusive use was used, and according to the product protocol of attachment to the kit, 1.0 µL of each reaction product was applied. In addition, for the peak analysis after electrophoresis, Agilent2100 expert software attached to the system was used, and waveform analysis and calculation of peak mobility were performed.

Figure 5:
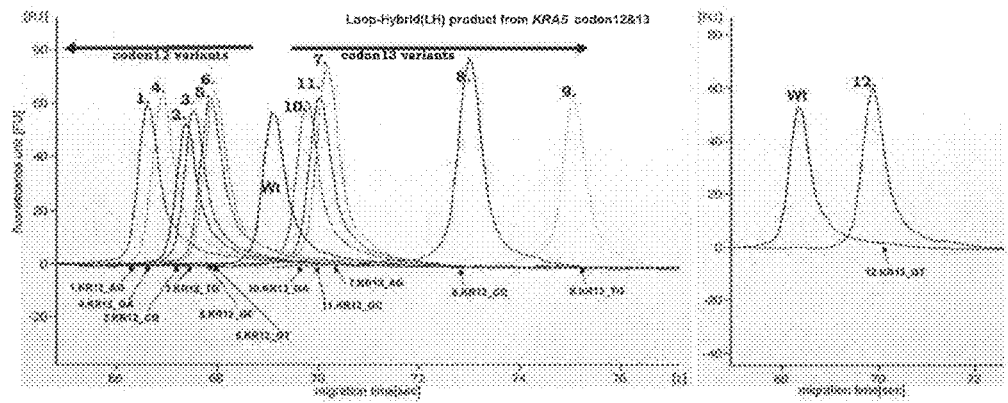
FIG. 5 is the result, obtained in Example 4, of electrophoresis carried out by microchip electrophoresis method for the hybrids of 12 kinds of mutant-type DNA and wild-type DNA of KRAS gene which were prepared by the LH method using the probe (IN-1) which forms the hybrid having the stem structure.

The results are shown in FIG. 5. In addition, the peak number in FIG. 5 expresses the product by the following probe: 1 expresses KR12_AG, 2 expresses KR12_CG, 3 expresses KR12_TG, 4 expresses KR12_GA, 5 expresses KR12_GC, 6 expresses KR12_GT, 7 expresses KR13_AG, 8 expresses KR13_CG, 9 expresses KR13_TG, 10 expresses KR13_GA, 11 expresses KR13_GC, and 12 expresses KR13_GT, respectively.

As is clear from the result shown in FIG. 5, when the detection was performed by microchip electrophoresis using the SLH reaction of the present invention, each peak of the mutant DNA which has mutation on a codon 12 and a codon 13 had separated from the peak of the wild-type DNA, and it turned out that the mutation was completely discriminable as a mutant-type DNA. That is, this result showed that mutant-type DNA obtained by the SLH reaction was easily detectable with microchip electrophoresis. The stem structure might be changed by generation of heat, however, it was considered that, because the electrophoresis was performed by microchip electrophoresis method with little generation of heat, stable structure could be maintained, and this made separation easy. Furthermore, it was shown that the microchip electrophoresis was suitable for detection of mutant-type DNA employing such SLH reaction since it is easy for peak analysis as compared with the gels electrophoresis.

In addition, like the KRAS gene testing, when mutation occurred in the adjacent codon (for example, codons 12 and 13), the mutations in both adjacent codons were needed to be detected. However, by the conventional loop hybrid method using the probe which forms only the loop structure (Del-7, etc.), all of the mutations in the adjacent codons could not be detected.

As is clear from the results shown in FIG. 5, by the method devised by the present inventors which employs the hybrid having the stem structure, it becomes possible to detect the mutations which may be generated in the adjacent codons 12 and 13 by the same measurement system with high precision.

Example 5: Detection of Mutant-Type DNA Having the Insertion Nucleotide Region of UGT1A1

The UGT1A1 gene has a promoter that contains a dinucleotide repeat: $(TA)_6$. (Referred to as (TA6)). A mutated form of the promoter contains an extra "TA" in the dinucleotide repeat sequence. Thus, the mutation variant has an expanded dinucleotide repeat: $(TA)_7$. (Referred to as (TA7)). In this example, a probe is designed that will bind to the wild-type or the mutation variant form of the UGT1A1 gene and induce the formation of a stem structure in the genomic DNA strand.

(1) Human Blood-Derived Genomic DNA and its Preparation

Multiple samples derived from human blood were prepared, and according to QIAGEN QIAamp DNA Blood Midi Kit, after treating 2 mL of each whole blood with proteinase K at 70° C. for 10 minutes, ethanol was added, and the supernatant solution after centrifugation was extracted and purified by QIAamp Midi column, and human genomic DNA was prepared. Using 50 ng of the genomic DNA as a template material, the sequence was determined by the same method as performed in Synthetic Example 1 (2). Three kinds of samples genotypes were identified: homozygous wild-type DNA (TA6), the heterozygous form with both the wild-type DNA (TA6) and mutant variant-type DNA (TA7), and the homozygous variant-type DNA (TA7), and used as samples.

(2) Preparation of the Probe for SLH Reaction

The following probe designed so that the stem structure might be formed on the genome sequence at the time of the hybrid formation was employed as the probe for SLH reaction (UGT1Adel-12F:

ctttgtggactgacagcttttatagtcacgtgacacagtcaaacattaac ttggtgtatcgattggttttgatataagtaggagagggcgaac [SEQ ID NO: 21]).

It should be noted that, when said probe [SEQ ID NO: 21] was used, it was conceived that the following stem structures formed in the genomic DNA strand amplified from the human blood sample that hybridized with probe [SEQ ID NO: 21], when subjected to the SLH reaction.

When the wild-type DNA (TA6) allele was present, the (TA6) portion of the gene formed the stem structure shown in FIG. 19.

When mutant-type DNA allele (TA7) was present, the (TA7) portion of the gene formed the stem structure shown in FIG. 20.

(3) SLH Reaction

Using three kinds of samples prepared in the above-described (1), the PCR reaction was performed using the AccuPrime Taq DNA Polymerase System (kit for the PCR reaction, produced by Invitrogen Corp.). That is, firstly, according to the product protocol of attachment to the kit, 1.0 µL of each 10 µM primer (ctttgtggactgacagcttttatag [SEQ ID NO: 19] and gctgccatccactgggatc [SEQ ID NO: 20]) and 2.0 µL of the PCR reaction buffer of attachment to the kit were used to prepare 20.0 µL of reaction liquid for PCR. Then, each 1 ng of human genomic DNA derived from normal human blood was added and suspended in 20 µL of reaction liquid for PCR, and used as a sample for PCR. In addition, for the oligo synthesis of the above-described primer and probe, custom synthesis service of Sigma-Genosys, Inc. was utilized. Using this sample for PCR, the PCR reaction of 36 cycles was performed with the use of DNA thermal cycler (DNA Engine PTC200, produced by MJ Research Inc.) on the following reaction condition.

| Reaction condition of the PCR: | |
|---|---|
| Thermal denaturation: | 95° C., 15 sec. |
| Annealing: | 55° C., 15 sec. |
| Polymerization reaction: | 68° C., 47 sec. |

After termination of the reaction, the SLH probe ID.=UGT1Adel-12F was added so that it gives a final concentration 200 nM, and then with the use of DNA Thermal Cycler of MJ Research Inc. (DNA Engine PTC200), 1 cycle of reaction was carried out on the following reaction condition.

| (SLH-reaction) | |
|---|---|
| PCR product | 4.5 µL |
| SLH probe | 0.5 µL, of 2 µM stock |
| 105° C. | hot lid |
| 95° C. | 2 min. |
| 55° C. | 30 sec. |
| 68° C. | 4 min. |
| 4° C. | pause |

(4) Separation and Detection of the Hybrid Generated by the SLH Reaction (Microchip Electrophoresis)

The SLH reaction product (hybrid) obtained in the above-described (3) was subjected to the microchip electrophoresis method with the use of Agilent 2100 Bioanalyzer systems (Agilent Technologies Inc.). In this electrophoresis method, Agilent DNA1000 Assay kit (produced by Agilent Technologies Inc.) which is the dedicated reagents was used, and according to the attached product protocol, 1.0 µL of each reaction products was applied. In addition, for peak analysis after electrophoresis, system attached Agilent 2100 Expert software was utilized, and waveform analysis and calculation of peak mobility were performed.

Figure 6:
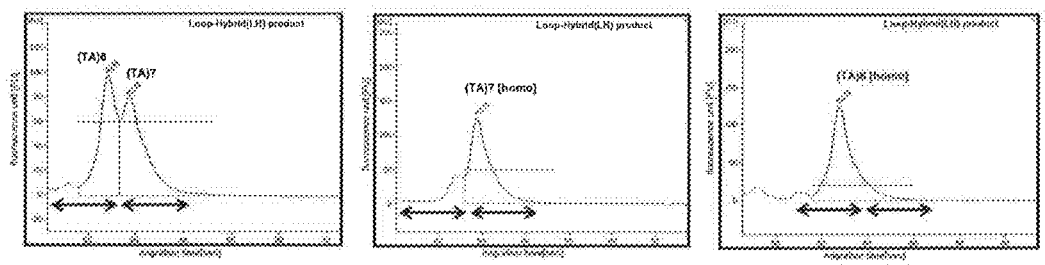
FIG. 6 shows the results, obtained in Example 5, of detection of the wild-type DNA (TA6) and mutant-type DNA (TA7) of UGT1A1 gene. Namely, the left panel shows the result of measurement of the hybrids prepared by the LH method for heterozygosity of the wild-type DNA (TA6) and mutant-type DNA (TA7); the middle panel shows the result of measurement of the hybrids prepared by the LH method for homozygosity of mutant-type DNA (TA7); and the right panel shows the result of measurement of the hybrids prepared by the LH method for the homo of the wild-type DNA (TA6), respectively.

The obtained results were shown in FIG. 6. In addition, in the figure, left panel shows the measurement result of the hetero of the wild-type DNA (TA6) and mutant-type DNA (TA7), middle panel shows the result of the homo of mutant-type DNA (TA7), and the right panel shows the result of the homo of the wild-type DNA (TA6), respectively.

As is clear from the result shown in FIG. 6, it turned out that according to the method of the present invention, discrimination and determination of genotype of gene polymorphism *28 of UGT1A1 gene promoter is enabled. That is, it turned out that even if it was a mutant-type DNA having an inserted nucleotide, the separation and detection of the wild-type DNA and the mutant-type DNA could be achieved by the method of the present invention. In addition, when the detection is a mutant gene which may form such hetero- and homozygosity, it was commonly difficult to detect the presence or absence of mutation and also to detect these genotypes with distinction, but it was confirmed that by employing the method of the present invention, the genotypes whether it is hetero- or homozygous could be discriminated clearly.

It should be noted that, with respect to UGT1A1 gene, in addition to the above-mentioned polymorphism *28, detection of polymorphism *6 of exon 1 will also be important. By subjecting the SLH reaction solutions of *6 and *28 to the same electrophoresis through the use of the method of the present invention, type determination of these polymorphism can be performed at the same time. Namely, fluorescent SLH probe for each polymorphism *6 and *28 were prepared, then hybridized with each *6 and *28, and the hybridized materials were mixed. By using this mixture as a sample for electrophoresis, only the interactant with SLH probe was detected specifically by the fluorescence of the probe and by setting a condition where these hybrids may separate by different mobility, discrimination of each genotype of respective polymorphism can be achieved by single trial.

Example 6: Specific Detection of LH Band for a Variant in UGT1A1 Polymorphism *28

The UGT1A1 gene may also be present in additional mutation variant forms. In one mutation variant form, a TA dinucleotide is deleted. The promoter contains one fewer dinucleotide repeat than the normal form: $(TA)_5$. (Referred to as (TA5)). Another mutated form of the promoter contains two extra "TA" dinucleotide sequences. Thus, the mutation variant has an expanded dinucleotide repeat: $(TA)_8$. (Referred to as (TA8)). In this example, a probe is designed that will bind to the wild-type or the mutation variant forms of the UGT1A1 gene and induce the formation of a stem structure in the genomic DNA strand.

(1) Preparation of Sample DNA which has a Sequence of Mutant-Type DNA and Wild-Type DNA in UGT1A1 Gene Using samples from 200 persons, screening was performed, and the wild-type DNA (TA6), as well as the mutant-type DNA in which with respect to wild type (TA6), locus *28 has variant alleles such as (TA5) (an allele in which one TA repeat is deleted from the wild-type allele), (TA7) (an allele in which one TA repeat was inserted in the wild-type allele), and (TA8) (an allele in which two TA repeats were inserted in the wild-type allele) were obtained and used as sample DNA.

Specifically, screening was carried out as follows. That is, the PCR reaction was carried out for each genomic DNA sample (5 ng) obtained from the samples derived from 200 persons in which locus *28 is heterozygous with one of those variant alleles using AccuprimeTaq (reaction condition: 95° C., 15 sec.; 55° C., 15 sec.; and 68° C., 47 sec., for 36 cycles). The obtained PCR amplification product was incorporated into TA cloning vector pCR2.1TOPO using TOPO® TA Cloning System (Invitrogen Corp.), and introduced into E. coli One Shot® TOP10 (Invitrogen Corp.) by electroporation. Then, the transfected E. coli was cultured in LB agar medium containing kanamycin (25 ng/mL) at 37° C. for 18 hours, and the colonies which acquired antibiotics resistance were selected as an indicator, and the obtained colony was cloned at random.

One loopful E. coli of each colony was cultured in 50 µL of liquid LB culture-medium containing 25 ng/mL ampicillin at 37° C. for 2 to 4 hours, and centrifuged. The bacterial precipitate after centrifugation was suspended by adding 8 µL of Green solution of Clone Checker (Invitrogen Corp.), and then DNA was released from fungal body by the heat shock at 98° C. for 30 seconds. This DNA solution was dispersed in 100 µL of distilled water, and it was amplified by TempliPhi (GE Healthcare), and then, sequence of the plasmid DNA was determined by Sanger method. By this screening, wild-type DNA (TA6), mutant-type DNA (TA5), mutant-type DNA (TA7), and mutant-type DNA (TA8) were obtained, and used as sample DNA.

(2) Preparation of the Probe for SLH Reaction

The following probe (UGT1Adel-8F), which was designed so that the stem structure could be formed on a genome sequence at the time of the hybrid formation, was synthesized.

[SEQ ID NO: 23]
ctttgtggactaacagcttttatagtcacgtgacacagtcaaacattaacttggtgtatcgattggttttgatatatataa
gtaggagagggcgaac When electrophoretic mobility of the hybrid was determined by detecting fluorescence of SYBRGreen I (SYBRGreen I), said probe (hereinafter, abbreviated as the probe 1) was used as the probe for SLH reaction. In addition, when electrophoretic mobility of the hybrid was determined by detecting fluorescence of Cy5, the one in which 5'-terminal of the sequence of aforementioned probe was modified with Cy5 (hereinafter, abbreviated as the probe 2) was used as the probe for SLH reaction. It should be noted that, as for fluorescent modification, custom synthesis service of Sigma-Genosys, Inc. was utilized.

When the above-described probes 1 and 2 were used, it was conceived that the following stem structures formed in the genome DNA strand amplified from the human blood sample that hybridized with probe [SEQ ID NO: 23], when subjected to the SLH reaction.

When mutant-type DNA allele (TA5) was present, the (TA5) portion of the gene formed the stem structure shown in FIG. 21.

Figure 22:
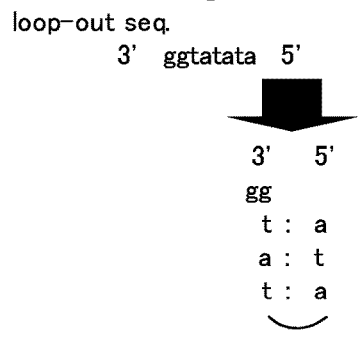

When the wild-type DNA (TA6) allele was present, the (TA6) portion of the gene formed the stem structure shown in FIG. 22.

Figure 23:
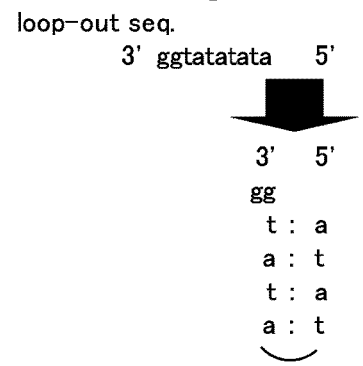

When mutant-type DNA allele (TA7) was present, the (TA7) portion of the gene formed the stem structure shown in FIG. 23.

Figure 24:
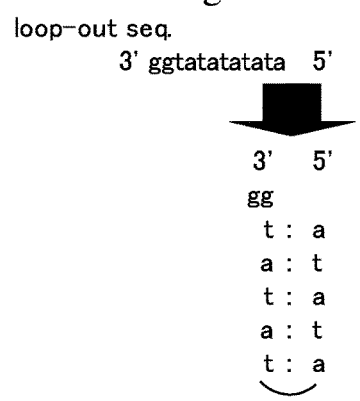

When mutant-type DNA allele (TA8) was present, the (TA8) portion of the gene formed the stem structure shown in FIG. 24.

(3) SLH Reaction

Using the four kinds of sample DNA prepared in the above-described (1), the PCR reaction for each sample was performed using the AccuPrime Taq DNA Polymerase System (a kit for the PCR reaction, produced by Invitrogen Corp.).

That is, first, according to the product protocol of attachment to the kit, 1.0 µL of each 10 µM primer (ctttgtggactgacagcttttatag [SEQ ID NO: 19]
and gctgccatccactgggatc [SEQ ID NO: 20])

and 2.0 µL of the PCR reaction buffer of attachment to the kit were used to prepare 20.0 µL of reaction liquid for PCR. Then, 1 ng of DNA sample was added and suspended in 20 µL of reaction solution for PCR, and used as a sample for PCR. It should be noted that, as for the oligo synthesis of the above-described primer and probe, custom synthesis service of Sigma-Genosys, Inc. was utilized. Using this sample for PCR, the PCR reaction of 36 cycles was performed with the use of DNA thermal cycler of MJ Research Inc. (DNA Engine PTC200) on the following reaction condition.

| Reaction condition of the PCR: | |
| --- | --- |
| Thermal denaturation: | 95° C., 15 sec. |
| Annealing: | 55° C., 15 sec. |
| Polymerization reaction: | 68° C., 47 sec. |

After termination of the reaction, the SLH probe 1 was added to each 4 kinds of obtained PCR products so that it gives a final concentration 200 nM, and then with the use of DNA Thermal Cycler of MJ Research Inc. (DNA Engine PTC200), 1 cycle of SLH reaction was carried out on the following reaction condition.

| (SLH-reaction:) | |
| --- | --- |
| PCR product | 4.5 µL |
| SLH probe | 0.5 µL of 2 µM stock |
| 105° C. | hot lid |
| 95° C. | 2 min. |
| 55° C. | 30 sec. |
| 68° C. | 4 min. |
| 4° C. | pause |

In addition, in the same manner as above, the SLH probe 2 was added to each 4 kinds of obtained PCR products so that it gives a final concentration 200 nM, and 1 cycle of SLH reaction was carried out on the above-described reaction condition.

(4) Separation and Detection of the Hybrid Generated by the SLH Reaction (Polyacrylamide Gel Electrophoresis)

To 1.5 µL of each 4 samples of the SLH reaction products (hybrid) obtained in the above-described (3) by using SLH probe 1, 1.5 µL of gel loading buffer was added respectively, and electrophoresis was performed in non-denaturing 10% polyacrylamide gel. In addition, as a molecular mass marker, 1.5 µL of 100 bp ladder for size marker (produced by Promega Corp.) was used and loaded on the same gel, and electrophoresed. The polyacrylamide gel used was a compact gel (Compact gel C10L, produced by ATTO Corp.) of 6 cm×6 cm, and electrophoresis was carried out by a small electrophoretic equipment (ATTO, AE-7300 Compact PAGE) using Tris-glycine buffer solution (37.5 mM Tris, 288 mM glycine) as a buffer solution for electrophoresis at room temperature. After the electrophoresis, gel was stained with SYBR Green I (TAKARA BIO Inc., F0513) for 10 minutes and washed with water, and then detection (excitation wavelength 635 nm, detection filter 650LP) was performed using a laser imaging scanner (Amersham Biosciences Corp., STORM 860). In this occasion, for the fluorescence detection of SYBR Green I, excitation wavelength of 450 nm, detection filter 520LP was utilized. The results obtained were shown in the left panel of FIG. 7. In addition, lane 1 shows the result obtained by use of mutant-type DNA (TA5); lane 2 shows the result obtained by the use of mutant-type DNA (TA6); lane 3 shows the result obtained by the use of mutant-type DNA (TA7); lane 4 shows the result obtained by the use of mutant-type DNA (TA8), respectively.

In addition, in the similar manner as above, using 1.5 µL of each 4 samples of the SLH reaction products (hybrid) obtained in the above-described (3) by using SLH probe 2, the electrophoresis was performed by the same way as described above, after that, fluorescence detection (excitation wavelength 635 nm, detection filter 650LP) was performed directly as it was. The results obtained were shown in the right panel of FIG. 7. It should be noted that, lane 1 expresses the result obtained by use of mutant-type DNA (TA5); lane 2 expresses the result obtained by use of wild-type DNA (TA6); lane 3 expresses the result obtained by use of mutant-type DNA (TA7); lane 4 expresses the result obtained by use of mutant-type DNA (TA8), respectively.

When the detection was performed by SYBR Green I (FIG. 7, left panel), the PCR band and LH band could also be confirmed, but other than these bands, other bands by the nonspecific amplification products which were assumed to emerge due to TA reiterated sequence were also seen. On the other hand, when detection was performed by Cy5 (FIG. 7, right panel), only LH probe and loop hybrid were seen predominantly. This was assumed that since the LH probe modified with Cy5 was employed, the amplification products which were not involve in the LH reaction were undetectable and only the one which hybridized with the LH probe were detected specifically. Thus, it turned out that by using the probe modified directly by coupling with a fluorescent group such as Cy5, more specific detection could be performed.

Figure 7:
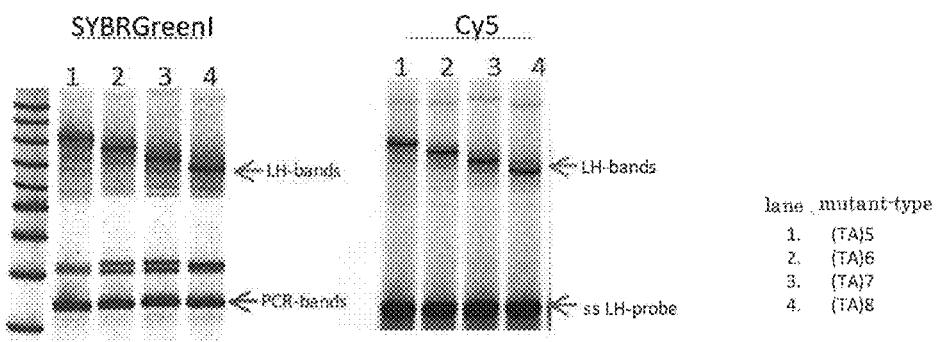
FIG. 7 shows the results, obtained in Example 6, of detection of the wild-type DNA (TA6) (lane 2) and mutant-type DNA (TA5) (lane 1), (TA7) (lane 3), and (TA8) (lane 4) of UGT1A1 gene. The left panel shows those measured by SYBR Green I fluorescence detection, and the right panel shows those measured by detection of Cy5 fluorescence.

In addition, as is clear from the results shown in FIG. 7, it also turned out that, according to the method of the present invention, the LH band for each wild-type DNA (TA6), mutant-type DNA (TA5), (TA7), and (TA8) were detected on the different position, therefore, these alleles could be differentiated in a single electrophoretic assay.

Example 7: Detection of Mutant-Type DNA Having the Insertion Nucleotide Region of UGT1A1 (Effect of Increased Times of LH Cycles on Amount of Loop Hybrid)

(1) Human Blood-Derived Human Genomic DNA and its Preparation

A 2 ml of human whole blood was processed by proteinase K at 70° C. for 10 minutes using QIAamp DNA Blood Midi Kit (QIAGEN Inc.). After that, ethanol was added thereto, and the supernatant solution after centrifugation was extracted and purified by QIAamp Midi column, and used it as a sample DNA.

A 50 ng of sample DNA was used as a template material, and the sequence determination was performed by the same method as performed in Synthetic example 1. As a result, it was confirmed that the sample was heterozygous for the UGT1A1 gene, having a wild-type DNA allele (TA6) and mutant-type DNA allele (TA7).

(2) Preparation of the Probe for SLH Reaction

The same probe as described Example 6 (2) was used. That is, the probe 1 was used for detecting fluorescence of SYBRGreen I (SYBRGreen I), and the probe 2 was used for detecting fluorescence of Cy5.

In addition, when said probes were used, it was conceived that the following stem structures formed in the DNA amplified from the human blood sample that hybridized with probe 1 or probe 2.

Figure 25:
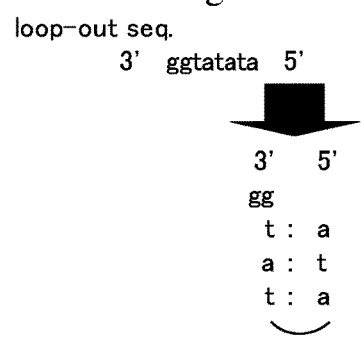

When the wild-type DNA allele was present, the (TA6) portion of the gene formed the stem structure shown in FIG. 25.

Figure 26:
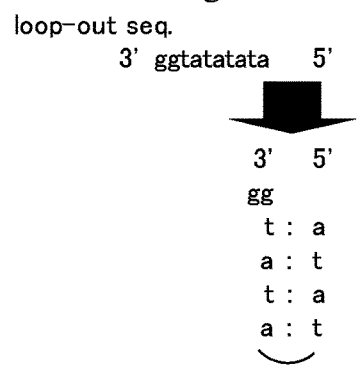

When mutant-type DNA allele (TA7) was present, the (TA7) portion of the gene formed the stem structure shown in FIG. 26.

(3) SLH Reaction

Using the sample DNA prepared in the above-described (1), the PCR reaction was performed in the same way as described in Example 6 (3).

After termination of the reaction, the SLH probe 1 was added to the obtained PCR product so that it gives a final concentration 200 nM, and then with the use of DNA Thermal Cycler of MJ Research Inc. (DNA Engine PTC200), 1 to 4 cycles of SLH reaction was carried out on the following reaction condition.

| (SLH-reaction:) | |
|---|---|
| PCR product | 4.5 µL |
| SLH probe | 0.5 µL of 2 µM stock |
| 105° C. | hot lid |
| 95° C. | 2 min. |
| 55° C. | 30 sec. |
| 68° C. | 4 min. |

In addition, in the same manner as above, the SLH probe 2 was added to the obtained PCR product so that it gives a final concentration 200 nM, and 1 to 4 cycles of SLH reaction was carried out on the above-described reaction condition.

(4) Separation and Detection of the Hybrid Generated by the SLH Reaction (Polyacrylamide Gel Electrophoresis)

Figure 8:
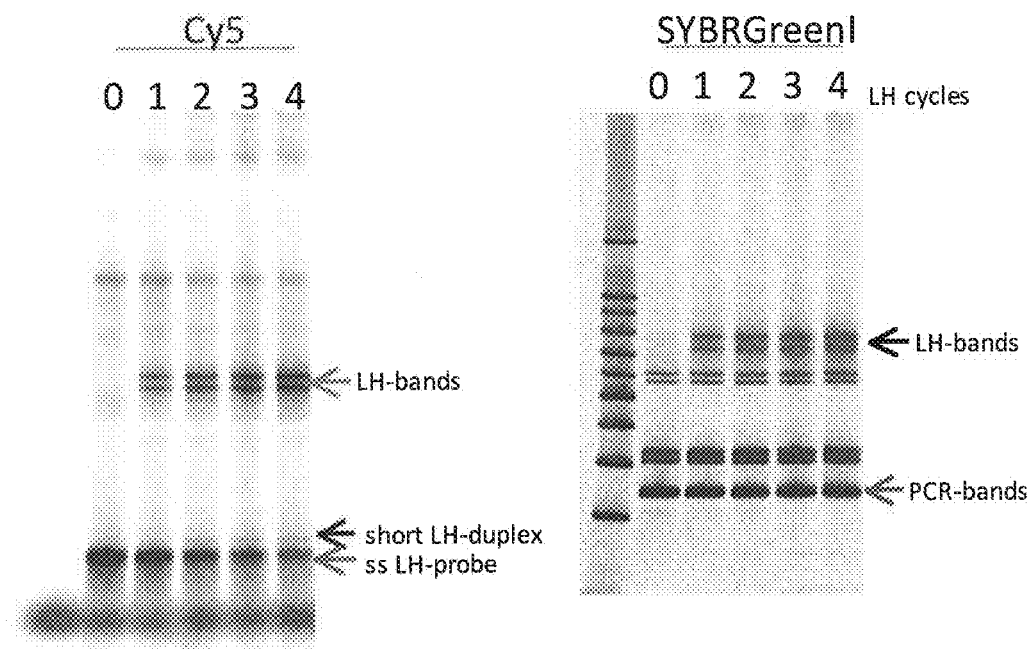
FIG. 8 is the figure, obtained in Example 7, which shows the result of detection of the wild-type DNA (TA6) and mutant-type DNA (TA7) of UGT1A1 gene after the LH cycle of 0 to 4 times. The left figure shows the result measured by fluorescence detection of Cy5; the right figure shows the result measured by fluorescence detection of SYBR Green I.

The SLH reaction products (hybrid) which were obtained in the above-described (3) by 1 to 4 cycles of the SLH reaction using the SLH probe 1 and PCR reaction product (0 cycle of SLH reaction) were prepared; and to 1.5 µL of each of them, 1.5 µL of gel loading buffer was added respectively, and electrophoresis was performed in a non-denaturing 10% polyacrylamide gel. As a molecular mass marker, 1.5 µL of 100 bp ladder for size marker (produced by Promega Corp.) was used, and loaded on the same gel and electrophoresed. The polyacrylamide gel used was a compact gel (Compact gel C10L, produced by ATTO Corp.) of 6 cm×6 cm, and electrophoresis was carried out by a small electrophoretic equipment (ATTO, AE-7300 Compact PAGE.) using Tris-glycine buffer solution (37.5 mM Tris, 288 mM glycine) as a buffer solution for electrophoresis at room temperature. After the electrophoresis, the gel was stained for 10 minutes with SYBR Green I (TAKARA BIO Inc., F0513), and washed with water, then detection was performed using a laser imaging scanner (Amersham Biosciences Corp., STORM 860). In this occasion, for the fluorescence detection of SYBR Green I, excitation wavelength of 450 nm, detection filter 520LP was utilized. The result obtained was shown in the right panel of FIG. 8. It should be noted that, lane 0 expresses the result obtained by the use of PCR reaction product, lane 1 to 4 expresses each result obtained by 1 to 4 cycles of SLH reaction.

In addition, in the similar manner as above, the SLH reaction products (hybrid) which were obtained in the above-described (3) by 1 to 4 cycles of the SLH reaction using the SLH probe 2 and PCR reaction product (0 cycle of SLH reaction) were prepared; and the electrophoresis was performed by the same way as described above, after that, fluorescence detection (excitation wavelength 635 nm, detection filter 650LP) was performed directly as it was. The result obtained was shown in the left panel of FIG. 8. In addition, lane 0 expresses the result obtained by the use of PCR reaction product, lane 1 to 4 expresses each result obtained by 1 to 4 cycles of SLH reaction.

In the left figure, the bands of SLH probe (ss LH-probe in the figure) and the loop hybrid (LH-bands in the figure) were seen remarkably, and it turned out that the amount of monomeric SLH probe was decreased while the amount of loop hybrids was increased with the increased times of SLH reaction cycles. Moreover, it was also confirmed that (TA6) and (TA7) appeared as separate bands (in LH-bands in the figure, the upper band was (TA6) and the lower band was (TA7)). In addition, in the results of electrophoresis of the hybrid obtained by 2 to 4 times of LH cycles, a new band was seen in slightly upward of the band of unbound LH probe, this was supposed to be a homoduplex which was created in the repeated SLH reaction using the primer region attached to the LH probe by elongation reaction with Taq polymerase along the genomic DNA template. Also, in the detection by SYBR Green I, it turned out that the amount of loop hybrid (LH-bands in the figure) was increased by increasing number of cycle of LH reaction. it turned out that in response to increase in number of times of LH cycle, the amount of loop hybrid (LH-bands in the figure) increased; and it was also confirmed that (TA6) and (TA7) appeared as separate bands.

Thus, as is clear from the above-described result, it turned out that the amount of loop hybrids was increased by increasing times of the LH reaction. It turned out that this was effective in a system with low loop hybrid formation rate, and especially, by carrying out 3 to 4 times, the hybrid can be obtained effectively. It should be noted that, although not shown in the figure, the result of 5 times of LH cycle was the almost same result as that of 4 times.

Example 8: Detection of Poly-T Chain Length Polymorphism in Nucleotide Sequence of TOMM40 Gene (Separation and Detection by the Hybrid Having the Stem Structure in the Both Side)

(1) Synthesis of Sample DNA Having a Fixed Poly-T Chain Length Corresponding to Various Poly-T Chain Length Polymorphisms in rs10524523 Marker Sequence of TOMM40 Gene As a model nucleotide sequence of poly-T chain length polymorphism (rs10524523) in TOMM40 gene, six kinds of sample DNA in the following table 3 were synthesized. In addition, Poly-T in the table corresponds to the chain length of poly-A.

TABLE 3

| Sample DNA | Sequence | SEQ ID NO: |
|---|---|---|
| Q10A (poly-T = 10) | taggcattcgaagccagcccgggcaacatggtgagaccc catctcAAAAAAAAAAgccagatgcaatggctcatg | [SEQ ID NO: 24] |
| Q15A (poly-T = 15) | taggcattcgaagccagcccgggcaacatggtgagaccc catctcAAAAAAAAAAAAAAAgccagatgca atggctcatg | [SEQ ID NO: 25] |

TABLE 3-continued

| Sample DNA | Sequence | SEQ ID NO: |
|---|---|---|
| Q20A (poly-T = 20) | taggcattcgaagccagcccgggcaacatggtgagaccc catctcAAAAAAAAAAAAAAAAAAAAgc cagatgcaatggctcatg | [SEQ ID NO: 26] |
| Q25A (poly-T = 25) | taggcattcgaagccagcccgggcaacatggtgagaccc catctcAAAAAAAAAAAAAAAAAAAAAAAA AAAAgccagatgcaatggctcatg | [SEQ ID NO: 27] |
| Q30A (poly-T = 30) | taggcattcgaagccagcccgggcaacatggtgagaccc catctcAAAAAAAAAAAAAAAAAAAAAA AAAAAAAAgccagatgcaatggctcatg | [SEQ ID NO: 28] |
| Q35A (poly-T = 35) | taggcattcgaagccagcccgggcaacatggtgagaccc catctcAAAAAAAAAAAAAAAAAAAAAA AAAAAAAAAAAAAgccagatgcaatggctc atg | [SEQ ID NO: 29] |

(2) Preparation of the Probe for SLH Reaction

The following probe (cy5delTINGC) which was designed to take the loop structure reflecting the number of nucleotide of the poly-T chain length on a genome sequence, and yet to take the stem structure on the probe in the hybrid formed by SLH reaction with target sequence was synthesized.

[SEQ ID NO: 30]
gacctcaagctgtcctcttgccccagccctccaaagcattgggattactggcatgagccattgcatctggacgcgcgt agatggggtctcaccatg In addition, in order to determine the hybrid by detecting fluorescence of Cy5, 5'-terminal of said probe sequence was fluorescence modified with Cy5 and employed as the probe for a SLH reaction. It should be noted that, as for fluorescent modification, custom synthesis service of Sigma-Genosys, Inc. was utilized.

Figure 27:
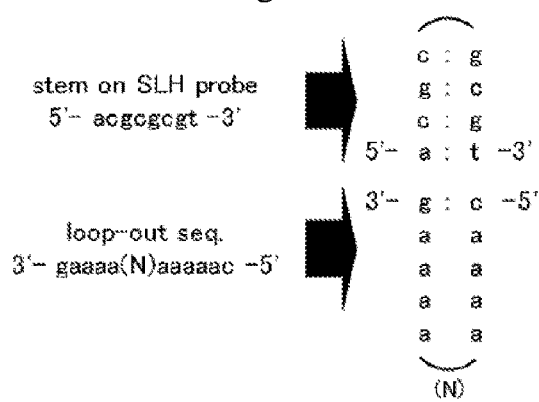

When aforementioned probe [SEQ ID NO: 30] was used, it was conceived that, by forming the hybrid with target genome sequence, such as any of [SEQ ID NO: 24-29], the stem-loop structure of the following structure should be formed (see scheme in FIG. 27). Thus, (N) in the scheme of FIG. 27 may represent different numbers of A nucleotides depending on the chain length of poly-T polymorphism. For example, if the genomic strand in the hybrid shown in the scheme of FIG. 27 has the sequence of [SEQ ID NO: 24], (N) represents two A nucleotides between the eight A nucleotides shown, and if the genomic strand's sequence was [SEQ ID NO: 29], then (N) represents twenty-seven A nucleotides.

(3) SLH Reaction

Using six kinds of sample DNA prepared in the above-described (1) as respective template DNA, and using the above-described cy5delTINGC as the probe for SLH, 4 cycles of the SLH reaction was performed.

Namely, to each 1.0 μL of 5 μM sample DNA (500 nM as concentration in reaction solution), respective 1.0 μL of 2 μM SLH probe (200 nM as concentration in reaction solution) was added, and after that, 0.04 μL of AccuPrime Taq DNA Polymerase High Fidelity (produced by Invitrogen Corp.), 1.0 μL of product attached 10× buffer, and 2.96 μL of dd H$_2$O were added respectively, and thus six kinds of respective 10 μL of reaction solution were prepared. Next, using six kinds of reaction solution, the SLH reaction of 4 cycles was performed with the thermal cycler of MJ Research Inc. (DNA Engine PTC200) on the following reaction condition.

| (SLH reactions cycling conditions) | |
|---|---|
| 105° C. | hot lid |
| 95° C. | 2 min. |

| -continued | |
|---|---|
| (SLH reactions cycling conditions) | |
| 55° C. | 15 sec. |
| 68° C. | 4 min. |

(4) Separation and Detection of the Hybrid Generated by the SLH Reaction (Polyacrylamide Gel Electrophoresis)

To 1.5 μL of each 5 samples of the SLH reaction products (hybrid product) obtained in the above-described (3) by using SLH probe, 1.5 μL of gel loading buffer was added respectively, and electrophoresis was performed in non-denaturing 10% polyacrylamide gel. In addition, as a molecular mass marker, 1.5 μL. of 100 bp ladder for size marker (produced by Promega Corp.) was used and loaded on the same gel, and electrophoresed. The polyacrylamide gel used was C-PAGEL (C10L, produced by ATTO Corp.) of 6 cm×6 cm, and electrophoresis was carried out by a small electrophoretic equipment (ATTO, AE-7300 Compact PAGE.) using Tris-glycine buffer solution (37.5 mM Tris, 288 mM glycine) as a buffer solution for electrophoresis at room temperature.

After the electrophoresis, fluorescence detection (excitation wavelength 635 nm, detection filter 650LP) was performed using a laser imaging scanner (Amersham Biosciences Corp., STORM 860). The results obtained were shown in FIG. 9.

Figure 9:
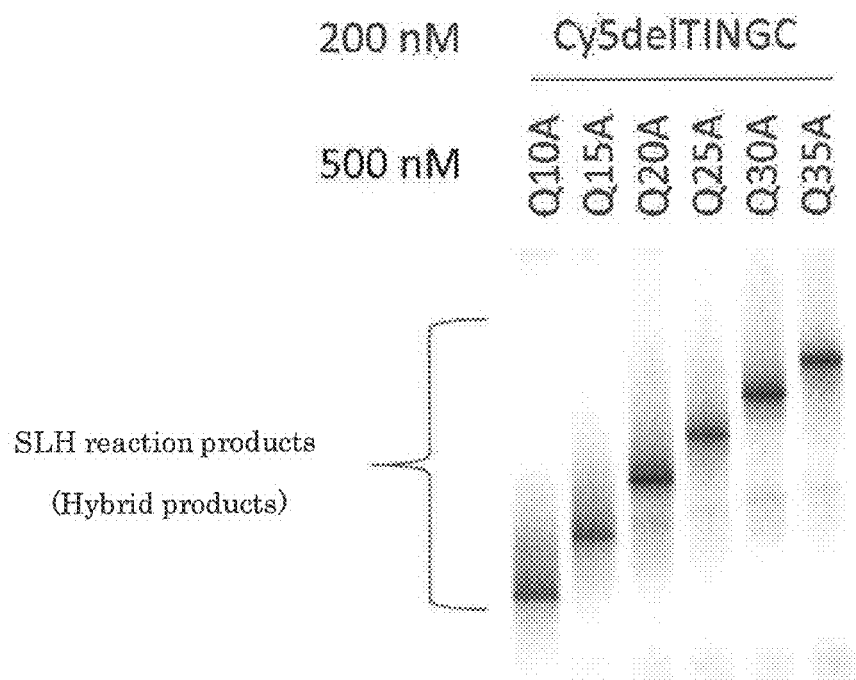
FIG. 9 is the figure, obtained in Example 8, which shows the result of detection of SLH formation to the amplified region DNA having fixed-length poly-T required to detect the poly-T polymorphisms in the TOMM40 gene, and its genotyping.

As is clear from the results shown in FIG. 9, as the result of performing separation by polyacrilamide gel electrophoresis and detection of the SLH reaction products obtained by the present invention using the above-described cy5delTINGC probe, it was shown that the detection to distinguish each sample DNA which are different by five nucleotides in the chain lengths of poly-T sequence could be performed. In addition, from these experimental results, showing high discriminatory performance between each sample, it could be anticipated that even if the difference by two nucleotides or even one nucleotide in poly-T sequence length, could well be detected. Here, taking clinical significance of diagnostic technique concerning TOMM40 gene polymorphism into consideration, the population with poly-T sequence chain length in the range of 11 to 16 nucleotides is classified as low risk group of onset of Alzheimer's disease, and the population in the range of 19 to 39 nucleotides, is discriminatory classified as a high-risk groups (The Pharmacogenomics Journal (2010) 10, 375-384). Therefore, the result shown in this Example has suggested that such performance can exceed the standard required for the diagnostic.

In addition, since polymorphism analysis of mono-, and di- or tri-nucleotide repeat have been difficult to be dealt with by conventional direct-sequencing method which is a in many cases, the simple and highly precise measurement technology by the present invention is highly useful.

SEQUENCE LISTING

The Sequence Listing text file named 10196-0025-01000_SEQUENCE_LISTING.txt, which has a creation date of Mar. 11, 2016, and a size of 8 kilobytes, is incorporated by reference herein in its entirety.

What is claimed is:

1. A method for detecting whether a wild-type nucleotide is substituted by a mutation nucleotide at a suspected mutated nucleotide site in a target DNA sequence, the method comprising:
   (1) providing a probe having a structure comprising $$3'\ \text{1stSS}_1\text{-X'}_1\text{-St}_{P1}\text{-X'}_2\text{-X'}_3\text{-X'}_4\text{-X'}_5\text{-2ndSS}_1\ 5';$$
   or
   $$3'\ \text{1stSS}_1\text{-X'}_1\text{-X'}_2\text{-X'}_3\text{-X'}_4\text{-St}_{P1}\text{-X'}_5\text{-2ndSS}_1\ 5';$$

wherein:
   the length of the probe is 30 to 300 nucleotides;
   $\text{1stSS}_1$ is a nucleotide sequence complementary to a portion of the target DNA sequence located on the 5' side of the suspected mutation site and $\text{2ndSS}_1$ is a nucleotide sequence complementary to a portion of the target DNA sequence located on the 3' side of the suspected mutation site;
   each of $X'_1$ and $X'_5$ independently represents a deoxyribonucleotide A, T, C, or G;
   each of $X'_2$, $X'_3$, and $X'_4$ independently represents a deoxyribonucleotide A, T, C, or G or a bond, wherein at most two of $X'_2$, $X'_3$, and $X'_4$ are the bond, and wherein one of $X'_2$, $X'_3$, and $X'_4$ is a deoxyribonucleotide A, T, C, or G which corresponds to the nucleotide of the suspected mutation nucleotide site and is complementary to the wild-type nucleotide when the suspected mutated nucleotide site contains the wild-type nucleotide; and
   $\text{Stp}_1$ is a nucleotide sequence of 4 to 60 nucleotides that is capable of forming a double-stranded stem structure of 2 to 20 base pairs when the probe is hybridized with the target DNA sequence;
   (2) contacting the probe with the sample containing the target DNA sequence in a solution under conditions capable of forming probe/target DNA sequence hybrids, wherein there is an electrophoretic mobility difference between the probe/target DNA sequence hybrids when the target DNA sequence has the wild-type nucleotide at the suspected mutated nucleotide site and the probe/target DNA sequence hybrids when the target DNA sequence has the mutation nucleotide at the suspected mutated nucleotide site;
   (3) analyzing the probe/target DNA sequence hybrids formed in step (2) by an electrophoresis which is performed under conditions in which there is an electrophoretic mobility difference between the probe/target DNA sequence hybrids when the target DNA sequence has the wild-type nucleotide at the suspected mutated nucleotide site and the probe/target DNA sequence hybrids when the target DNA sequence has the mutation nucleotide at the suspected mutated nucleotide site, thereby obtaining an electrophoresis analysis result; and
   (4) determining whether the wild-type nucleotide is substituted by the mutation nucleotide at the suspected mutated nucleotide site in the target DNA sequence in the sample by comparing the electrophoresis analysis result of step (3) with a first electrophoresis analysis result when the target DNA sequence has the wild-type nucleotide at the suspected mutation site or/and a second electrophoresis analysis result when the target DNA sequence has the mutation nucleotide at the suspected mutation site, wherein the first electrophoresis analysis result or/and the second electrophoresis analysis result is/are obtained by performing steps (1), (2) and (3).

2. The method according to claim 1, further comprises subjecting a solution containing the probe and the target DNA sequence to thermal denaturation conditions and template elongation conditions.

3. The method according to claim 1, wherein said contacting the probe with the sample comprises performing 1 to 4 cycles of: (i) heating the solution at 90° C. to 100° C. and (ii) heating the solution at 65° C. to 75° C.

4. The method according to claim 1, wherein said contacting the probe with the sample comprises performing 1 to 4 cycles of: (i) heating the solution at 90° C. to 100° C., (ii) heating the solution at 30° C. to 55° C., and (iii) heating the solution at 65° C. to 75° C.

5. The method according to claim 1, wherein the electrophoresis is microchip electrophoresis or capillary gel electrophoresis.

6. The method according to claim 1, wherein $X'_1$ is complementary to its corresponding nucleotide in the target DNA sequence and $X'_5$ is complementary to its corresponding nucleotide in the target DNA sequence.

7. The method according to claim 1, wherein $St_{P1}$ is a nucleotide sequence further capable of forming a loop structure when the probe is hybridized with the target DNA sequence.

8. The method according to claim 1, wherein the DNA target sequence in the probe/target DNA sequence hybrids forms a loop structure and/or a stem structure.

9. A method for detecting whether a wild-type nucleotide is substituted by a mutation nucleotide at a suspected mutated nucleotide site in a target DNA sequence in a sample, the method comprising:
(1) providing a probe having a structure comprising $$3'\ 1stSS_{331}\text{-}X'_{331}\text{-}IM'_{331}\text{-}Stp_{331}\text{-}X'_{332}\text{-}2ndSS_{331}\ 5',$$
or
$$3'\ 1stSS_{331}\text{-}X'_{331}\text{-}Stp_{331}\text{-}IM'_{331}\text{-}X'_{332}\text{-}2ndSS_{331}\ 5'$$

wherein:
the length of the probe is 30 to 300 nucleotides;
$1stSS_1$ is a nucleotide sequence complementary to a portion of the target DNA sequence located on the 5' side of the suspected mutation site and $2ndSS_1$ is a nucleotide sequence complementary to a portion of the target DNA sequence located on the 3' side of the suspected mutation site;
each of $X'_1$ and $X'_5$ independently represents a deoxyribonucleotide A, T, C, or G;
each of $X'_2$, $X'_3$, and $X'_4$ independently represents a deoxyribonucleotide A, T, C, or G or a bond, wherein at most two of $X'_2$, $X'_3$, and $X'_4$ are the bond, and wherein one of $X'_2$, $X'_3$, and $X'_4$ is a deoxyribonucleotide A, T, C, or G which corresponds to the nucleotide of the suspected mutation nucleotide site and is complementary to the mutation nucleotide when the suspected mutated nucleotide site contains the mutation nucleotide; and
$Stp_1$ is a nucleotide sequence of 4 to 60 nucleotides that is capable of forming a double-stranded stem structure of 2 to 20 base pairs when the probe is hybridized with the target DNA sequence;
(2) contacting the probe with the sample containing the target DNA sequence in a solution under conditions capable of forming probe/target DNA sequence hybrids, wherein there is an electrophoretic mobility difference between the probe/target DNA sequence hybrids when the target DNA sequence has the wild-type nucleotide at the suspected mutated nucleotide site and the probe/target DNA sequence hybrids when the target DNA sequence has the mutation nucleotide at the suspected mutated nucleotide site;
(3) analyzing the probe/target DNA sequence hybrids formed in step (2) by an electrophoresis which is performed under conditions in which there is an electrophoretic mobility difference between the probe/target DNA sequence hybrids when the target DNA sequence has the wild-type nucleotide at the suspected mutated nucleotide site and the probe/target DNA DNA sequence hybrids when the target DNA sequence has the mutation nucleotide at the suspected mutated nucleotide site, thereby obtaining an electrophoresis analysis result; and
(4) determining whether the wild-type nucleotide is substituted by the mutation nucleotide at the suspected mutated nucleotide site in the target DNA sequence in the sample by comparing the electrophoresis analysis result of step (3) with a first electrophoresis analysis result when the target DNA sequence has the wild-type nucleotide at the suspected mutation site or/and a second electrophoresis analysis result when the target DNA sequence has the mutation nucleotide at the suspected mutation site, wherein the first electrophoresis analysis result or/and the second electrophoresis analysis result is/are obtained by performing steps (1), (2) and (3).

10. The method according to claim 9, further comprises subjecting a solution containing the probe and the target DNA sequence to thermal denaturation conditions and template elongation conditions.

11. The method according to claim 9, wherein said contacting the probe with the sample comprises performing 1 to 4 cycles of: (i) heating the solution at 90° C. to 100° C. and (ii) heating the solution at 65° C. to 75° C.

12. The method according to claim 9, wherein said contacting the probe with the sample comprises performing 1 to 4 cycles of: (i) heating the solution at 90° C. to 100° C., (ii) heating the solution at 30° C. to 55° C., and (iii) heating the solution at 65° C. to 75° C.

13. The method according to claim 9, wherein the electrophoresis is microchip electrophoresis or capillary gel electrophoresis.

14. The method according to claim 9, wherein $X'_1$ is complementary to its corresponding nucleotide in the target DNA sequence and $X'_5$ is complementary to its corresponding nucleotide in the target DNA sequence.

15. The method according to claim 9, wherein $St_{P1}$ is a nucleotide sequence further capable of forming a loop structure when the probe is hybridized with the target DNA sequence.

* * * * *

UNITED STATES PATENT AND TRADEMARK OFFICE
CERTIFICATE OF CORRECTION

PATENT NO. : 9,834,813 B2
APPLICATION NO. : 13/825223
DATED : December 5, 2017
INVENTOR(S) : Shoichi Matsukuma et al.

Page 1 of 1

It is certified that error appears in the above-identified patent and that said Letters Patent is hereby corrected as shown below:

In the Claims

In Claim 9, at Column 65, Lines 16-22, please replace:
"(1) providing a probe having a structure comprising
3' 1stSS$_{331}$-X'$_{331}$-IM'$_{331}$-Stp$_{331}$-X'$_{332}$-2ndSS$_{331}$ 5',
or
3' 1stSS$_{331}$-X'$_{331}$-Stp$_{331}$-IM'$_{331}$-X'$_{332}$- 2ndSS$_{331}$ 5'"

With:
--(1) providing a probe having a structure comprising
3' 1stSS$_1$-X'$_1$-St$_{P1}$-X'$_2$-X'$_3$-X'$_4$-X'$_5$-2ndSS$_1$ 5'; or
3' 1stSS$_1$-X'$_1$-X'$_2$-X'$_3$-X'$_4$-St$_{P1}$-2ndSS$_1$ 5';--

Signed and Sealed this
Twelfth Day of March, 2019

Andrei Iancu
*Director of the United States Patent and Trademark Office*

```
                       SEQUENCE LISTING

<160> NUMBER OF SEQ ID NOS: 38

<210> SEQ ID NO 1
  <211> LENGTH: 22
  <212> TYPE: DNA
  <213> ORGANISM: Artificial Sequence
  <220> FEATURE:
  <223> OTHER INFORMATION: primer

<400> SEQUENCE: 1
catgaaaatg gtcagagaaa cc                                              22

<210> SEQ ID NO 2
  <211> LENGTH: 20
  <212> TYPE: DNA
  <213> ORGANISM: Artificial Sequence
  <220> FEATURE:
  <223> OTHER INFORMATION: primer

<400> SEQUENCE: 2
acttgtggta gttggagctc                                                 20

<210> SEQ ID NO 3
  <211> LENGTH: 20
  <212> TYPE: DNA
  <213> ORGANISM: Artificial Sequence
  <220> FEATURE:
  <223> OTHER INFORMATION: primer

<400> SEQUENCE: 3
acttgtggta gttggagctt                                                 20

<210> SEQ ID NO 4
  <211> LENGTH: 20
  <212> TYPE: DNA
  <213> ORGANISM: Artificial Sequence
  <220> FEATURE:
  <223> OTHER INFORMATION: primer

<400> SEQUENCE: 4
acttgtggta gttggagcta                                                 20

<210> SEQ ID NO 5
  <211> LENGTH: 20
  <212> TYPE: DNA
  <213> ORGANISM: Artificial Sequence
  <220> FEATURE:
  <223> OTHER INFORMATION: primer

<400> SEQUENCE: 5
cttgtggtag ttggagctgc                                                 20
```

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
cttgtggtag ttggagctgt                                        20

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
cttgtggtag ttggagctga                                        20

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
tgtggtagtt ggagctggtc                                        20

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
tgtggtagtt ggagctggtt                                        20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
tgtggtagtt ggagctggta                                        20

<210> SEQ ID NO 11
<211> LENGTH: 21
<212> TYPE: DNA
<213> ORGANISM: Artificial Sequence
<220> FEATURE:
<223> OTHER INFORMATION: primer

<400> SEQUENCE: 11
ggagctggtg ccgtaggcaa g                                      21

<210> SEQ ID NO 12
<211> LENGTH: 20
<212> TYPE: DNA
<213> ORGANISM: Artificial Sequence
<220> FEATURE:

```
<223> OTHER INFORMATION: primer

<400> SEQUENCE: 12
gtggtagttg gagctggtgt                                                    20

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
gtggtagttg gagctggtga                                                    20

<210> SEQ ID NO 14
<211> LENGTH: 24
<212> TYPE: DNA
<213> ORGANISM: Artificial Sequence
<220> FEATURE:
<223> OTHER INFORMATION: primer

<400> SEQUENCE: 14
gtactggtgg agtatttgat agtg                                               24

<210> SEQ ID NO 15
<211> LENGTH: 22
<212> TYPE: DNA
<213> ORGANISM: Artificial Sequence
<220> FEATURE:
<223> OTHER INFORMATION: primer

<400> SEQUENCE: 15
ggtcctgcac cagtaatatg ca                                                 22

<210> SEQ ID NO 16
<211> LENGTH: 21
<212> TYPE: DNA
<213> ORGANISM: Artificial Sequence
<220> FEATURE:
<223> OTHER INFORMATION: primer

<400> SEQUENCE: 16
aaggcctgct gaaaatgact g                                                  21

<210> SEQ ID NO 17
<211> LENGTH: 89
<212> TYPE: DNA
<213> ORGANISM: Artificial Sequence
<220> FEATURE:
<223> OTHER INFORMATION: probe

<400> SEQUENCE: 17
aaggcctgct gaaaatgact gaatataaac ttgtggtagt tggagctggt atatatatag        60
gcgtaggcaa gagtgccttg acgatacag                                          89

<210> SEQ ID NO 18
<211> LENGTH: 82
<212> TYPE: DNA
<213> ORGANISM: Artificial Sequence
<220> FEATURE:
<223> OTHER INFORMATION: probe

<400> SEQUENCE: 18
aaggcctgct gaaaatgact gaatataaac ttgtggtagt tggagctggt ggcgtaggca        60
```
agagtgcctt gacgatacag ct                                                    82

<210> SEQ ID NO 19
<211> LENGTH: 26
<212> TYPE: DNA
<213> ORGANISM: Artificial Sequence
<220> FEATURE:
<223> OTHER INFORMATION: primer

<400> SEQUENCE: 19
ctttgtggac tgacagcttt ttatag                                                26

<210> SEQ ID NO 20
<211> LENGTH: 19
<212> TYPE: DNA
<213> ORGANISM: Artificial Sequence
<220> FEATURE:
<223> OTHER INFORMATION: primer

<400> SEQUENCE: 20
gctgccatcc actgggatc                                                        19

<210> SEQ ID NO 21
<211> LENGTH: 95
<212> TYPE: DNA
<213> ORGANISM: Artificial Sequence
<220> FEATURE:
<223> OTHER INFORMATION: probe

<400> SEQUENCE: 21
ctttgtggac tgacagcttt ttatagtcac gtgacacagt caaacattaa cttggtgtat          60
cgattggttt tgatataag taggagaggg cgaac                                      95

<210> SEQ ID NO 22
<211> LENGTH: 87
<212> TYPE: DNA
<213> ORGANISM: Artificial Sequence
<220> FEATURE:
<223> OTHER INFORMATION: probe

<400> SEQUENCE: 22
aaggcctgct gaaaatgact gaatataaac ttgtggtagt tggagctggt tctgcagaag          60
gtgtaggcaa gagtgccttg acgatac                                              87

<210> SEQ ID NO 23
<211> LENGTH: 99
<212> TYPE: DNA
<213> ORGANISM: Artificial Sequence
<220> FEATURE:
<223> OTHER INFORMATION: probe

<400> SEQUENCE: 23
ctttgtggac tgacagcttt ttatagtcac gtgacacagt caaacattaa cttggtgtat          60
cgattggttt tgatatata taagtaggag agggcgaac                                  99

<210> SEQ ID NO 24
<211> LENGTH: 75
<212> TYPE: DNA
<213> ORGANISM: Artificial Sequence
<220> FEATURE:
<223> OTHER INFORMATION: modified DNA

<400> SEQUENCE: 24
taggcattcg aagccagccc gggcaacatg gtgagacccc atctcaaaaa aaaaagccag    60
atgcaatggc tcatg    75

<210> SEQ ID NO 25
<211> LENGTH: 80
<212> TYPE: DNA
<213> ORGANISM: Artificial Sequence
<220> FEATURE:
<223> OTHER INFORMATION: modified DNA

<400> SEQUENCE: 25
taggcattcg aagccagccc gggcaacatg gtgagacccc atctcaaaaa aaaaaaaaaa    60
gccagatgca atggctcatg    80

<210> SEQ ID NO 26
<211> LENGTH: 85
<212> TYPE: DNA
<213> ORGANISM: Artificial Sequence
<220> FEATURE:
<223> OTHER INFORMATION: modified DNA

<400> SEQUENCE: 26
taggcattcg aagccagccc gggcaacatg gtgagacccc atctcaaaaa aaaaaaaaaa    60
aaaaagccag atgcaatggc tcatg    85

<210> SEQ ID NO 27
<211> LENGTH: 90
<212> TYPE: DNA
<213> ORGANISM: Artificial Sequence
<220> FEATURE:
<223> OTHER INFORMATION: modified DNA

<400> SEQUENCE: 27
taggcattcg aagccagccc gggcaacatg gtgagacccc atctcaaaaa aaaaaaaaaa    60
aaaaaaaaaa gccagatgca atggctcatg    90

<210> SEQ ID NO 28
<211> LENGTH: 95
<212> TYPE: DNA
<213> ORGANISM: Artificial Sequence
<220> FEATURE:
<223> OTHER INFORMATION: modified DNA

<400> SEQUENCE: 28
taggcattcg aagccagccc gggcaacatg gtgagacccc atctcaaaaa aaaaaaaaaa    60
aaaaaaaaaa aaaaagccag atgcaatggc tcatg    95

<210> SEQ ID NO 29
<211> LENGTH: 100
<212> TYPE: DNA
<213> ORGANISM: Artificial Sequence
<220> FEATURE:
<223> OTHER INFORMATION: modified DNA

<400> SEQUENCE: 29
taggcattcg aagccagccc gggcaacatg gtgagacccc atctcaaaaa aaaaaaaaaa    60
aaaaaaaaaa aaaaaaaaaa gccagatgca atggctcatg    100

<210> SEQ ID NO 30
<211> LENGTH: 96
<212> TYPE: DNA
<213> ORGANISM: Artificial Sequence

```
<220> FEATURE:
<223> OTHER INFORMATION: probe

<400> SEQUENCE: 30
gacctcaagc tgtcctcttg ccccagccct ccaaagcatt gggattactg gcatgagcca    60
ttgcatctgg acgcgcgtag atggggtctc accatg                              96

<210> SEQ ID NO 31
<211> LENGTH: 21
<212> TYPE: DNA
<213> ORGANISM: Artificial Sequence
<220> FEATURE:
<223> OTHER INFORMATION: probe

<400> SEQUENCE: 31
ggtatatata taggcccacc g                                              21

<210> SEQ ID NO 32
<211> LENGTH: 21
<212> TYPE: DNA
<213> ORGANISM: Artificial Sequence
<220> FEATURE:
<223> OTHER INFORMATION: probe

<400> SEQUENCE: 32
cgtatatata taggcccacc g                                              21

<210> SEQ ID NO 33
<211> LENGTH: 21
<212> TYPE: DNA
<213> ORGANISM: Artificial Sequence
<220> FEATURE:
<223> OTHER INFORMATION: probe

<400> SEQUENCE: 33
tgtatatata taggcccacc g                                              21

<210> SEQ ID NO 34
<211> LENGTH: 21
<212> TYPE: DNA
<213> ORGANISM: Artificial Sequence
<220> FEATURE:
<223> OTHER INFORMATION: probe

<400> SEQUENCE: 34
gatatatata taggcccacc g                                              21

<210> SEQ ID NO 35
<211> LENGTH: 21
<212> TYPE: DNA
<213> ORGANISM: Artificial Sequence
<220> FEATURE:
<223> OTHER INFORMATION: probe

<400> SEQUENCE: 35
gctatatata taggcccacc g                                              21

<210> SEQ ID NO 36
<211> LENGTH: 21
<212> TYPE: DNA
<213> ORGANISM: Artificial Sequence
<220> FEATURE:
<223> OTHER INFORMATION: probe

<400> SEQUENCE: 36
```

```
gttatatata taggcccacc g                                              21

<210> SEQ ID NO 37
<211> LENGTH: 21
<212> TYPE: DNA
<213> ORGANISM: Artificial Sequence
<220> FEATURE:
<223> OTHER INFORMATION: probe

<400> SEQUENCE: 37
ggtatatata tacgcccacc g                                              21

<210> SEQ ID NO 38
<211> LENGTH: 21
<212> TYPE: DNA
<213> ORGANISM: Artificial Sequence
<220> FEATURE:
<223> OTHER INFORMATION: probe

<400> SEQUENCE: 38
ggtatatata tatgcccacc g                                              21
```